(12) United States Patent
Sebti et al.

(10) Patent No.: US 8,993,760 B2
(45) Date of Patent: Mar. 31, 2015

(54) ROCK INHIBITORS AND USES THEREOF

(75) Inventors: Said M. Sebti, Tampa, FL (US); Andrew D. Hamilton, New Haven, CT (US)

(73) Assignees: University of South Florida, Tampa, FL (US); Yale University, New Haven, CT (US)

(*) Notice: Subject to any disclaimer, the term of this patent is extended or adjusted under 35 U.S.C. 154(b) by 821 days.

(21) Appl. No.: 12/488,826

(22) Filed: Jun. 22, 2009

(65) Prior Publication Data

US 2009/0318684 A1 Dec. 24, 2009

Related U.S. Application Data

(63) Continuation of application No. PCT/US2007/088316, filed on Dec. 20, 2007.

(60) Provisional application No. 60/871,026, filed on Dec. 20, 2006.

(51) Int. Cl.

| C07D 401/04 | (2006.01) |
| C07D 401/06 | (2006.01) |
| C07D 217/02 | (2006.01) |
| C07D 241/08 | (2006.01) |
| C07D 401/12 | (2006.01) |

(52) U.S. Cl.
CPC ............ *C07D 401/04* (2013.01); *C07D 217/02* (2013.01); *C07D 241/08* (2013.01); *C07D 401/06* (2013.01); *C07D 401/12* (2013.01)
USPC ..................................................... 544/360

(58) Field of Classification Search
None
See application file for complete search history.

(56) References Cited

U.S. PATENT DOCUMENTS

| 4,179,337 | A | 12/1979 | Davis et al. | |
| 6,344,449 | B1 * | 2/2002 | Rudolf et al. | 514/211.05 |
| 6,906,061 | B2 | 6/2005 | Uehata et al. | |
| 2002/0035243 | A1 | 3/2002 | Imfeld et al. | |
| 2002/0120100 | A1 | 8/2002 | Bonny | |
| 2003/0032594 | A1 | 2/2003 | Bonny | |
| 2005/0182102 | A1 | 8/2005 | Hong et al. | |
| 2006/0116382 | A1 * | 6/2006 | Yao et al. | 514/253.04 |
| 2006/0142313 | A1 | 6/2006 | Nagarathnam et al. | |
| 2006/0258672 | A1 * | 11/2006 | Barbosa et al. | 514/253.01 |

FOREIGN PATENT DOCUMENTS

| JP | 62255479 | * | 11/1987 | ........... C07D 213/74 |
| WO | 02088093 | * | 11/2002 | ........... C07D 235/06 |
| WO | WO 2006010751 | * | 2/2006 | ........... C07D 213/74 |

OTHER PUBLICATIONS

Richards et al. Bioorganic and Medicinal Chemistry Letters, 2006, 16(24), pp. 6421-6425.*
Breitenlechner, et al., Protein Kinase A in Complex with Rho-Kinase Inhibitors Y-27632, Fasudil, and H-1152P: Structural Basis of Selectivity, Structure, 2003, vol. 11, pp. 1595-1607.
Liu, et al., A Novel and Facile Method to Synthesize (R)- and (S)-2-Methylpiperazine, Synthetic Communications, 2004, vol. 34, No. 22, pp. 4111-4118.
Jacobs, et al., The Structure of Dimeric ROCK I Reveals the Mechanism for Ligand Selectivity, Journal of Biological Chemistry, 2006, vol. 281, No. 1, pp. 260-268.
Amano, et al., Regulation and Functions of Rho-Associated Kinase, Experimental Cell Research, 2000, vol. 261, pp. 44-51.
Matsui, et al., Rho-Associated Kinase, a Novel Serine/Threonine Kinase, as a Putative Target for the Small GTP Binding Protein Rho, EMBO Journal, 1996, vol. 15, No. 9, pp. 2208-2216.
Li, et al., Inhibition of Protein Geranylgeranylation and RhoA/RhoA Kinase Pathway Induces Apoptosis in Human Endothelial Cells, Journal of Biological Chemistry, 2002, vol. 277, No. 18, pp. 15309-15316.
Adnane, et al., RhoB, Not RhoA, Represses the Transcription of the Transforming Growth Factor Beta Type II Receptor by a Mechanism Involving Activator Protein 1, Journal of Biological Chemistry, 2002, vol. 277, No. 10, pp. 8500-8507.

* cited by examiner

*Primary Examiner* — Noble Jarrell
(74) *Attorney, Agent, or Firm* — Robert J. Varkonyi; Smith & Hopen, P.A.

(57) ABSTRACT

The subject invention concerns compositions and methods for blocking cancer cell growth or proliferation and/or inducing cancer cell death. Compositions of the present invention are compounds that inhibit Rho-protein associated kinase function. Compounds of the invention include piperazinyl pyridines, piperazinylmethyl pyridines, piperazinyl ureas and carbamates, piperazinyl pyridines and quinoilines (including isoquinliones) as well as piperazinyl (including piperazinylmethyl) pyridines and quinolines (including isoquinolines). Compounds of the invention disrupt Rho-kinase activation and function and significantly inhibit tumor cell growth and induce tumor cell death.

7 Claims, 18 Drawing Sheets

Rho kinase Inhibition Assay

| Compounds | Testing Conc. (μM) | % Inhibition |
|---|---|---|
| H-1152 | 0.1 | 80 |
| Y-27632 | 0.5 | 55 |
| 1a | 100 | 29 |
| 1b | | 29 |
| 1c | | 27 |
| 1d | | 25 |
| 1e | | 23 |
| 1f | | 21 |

ROCK INHIBITORS AND USES THEREOF

CROSS REFERENCE TO RELATED APPLICATIONS

This application is a continuation of prior filed International Application, Serial Number PCT/US2007/088316 filed Dec. 20, 2007, which claims priority to U.S. provisional patent application No. 60/871,026 filed Dec. 20, 2006 which is hereby incorporated by reference into this disclosure.

STATEMENT OF GOVERNMENT INTEREST

This invention was made with Government support under Grant No. U19 CA067771 awarded by the National Institutes of Health. The Government has certain rights in the invention.

FIELD OF INVENTION

This invention relates to materials and methods for blocking tumor growth and inducing tumor cell death by disrupting the activity of Rho-associated protein kinases.

BACKGROUND OF THE INVENTION

Rho GTPase is a small G-protein which plays a critical role in signaling pathways and controls cell growth and division. A molecular switch control modifications in the actin cytoskeleton during cell proliferation, transformation, migration and morphogenesis. Rho must be located at the interior of plasma membrane and is translocated by attachment of C-20 geranyl geranyl group to a C-terminal. GTP bound form Rho is "switched on" and interacts with a variety of downstream effectors such as "Rho Kinase."

Rho-associated protein kinase is known as ROCK or Rho kinase, Ser/Thr protein kinase and is activated by GTP bound Rho, then phosphorylate and transduce the cell signals. Rho/Rho-Kinase signaling pathways are implicated in cell morphology, motility, smooth muscle contraction, formation of stress fiber, focal adhesion, cell transformation, and cytokineses.

SUMMARY OF INVENTION

The subject invention concerns compositions and methods for blocking cancer cell growth or proliferation and/or inducing cancer cell death. Compositions of the present invention are compounds that inhibit Rho-associated protein associated kinase function. Compounds of the invention include piperazinyl pyridines, piperazinylmethylpyridines, piperazinyl ureas and carbamates, piperazinyl pyridines and quinoilines (including isoquinliones) as well as piperazinyl (including piperazinylmethyl)pyridines and quinolines (including isoquinolines). Compounds of the invention disrupt Rho-kinase activation and function and significantly inhibit tumor cell growth and induce tumor cell death.

BRIEF DESCRIPTION OF THE DRAWINGS

For a fuller understanding of the invention, reference should be made to the following detailed description, taken in connection with the accompanying drawings:

FIG. 8 is a graph showing the effectiveness of IP-IV67 as a ROCK 1 inhibitor (results of 4 experiments shown).

DETAILED DESCRIPTION OF THE PREFERRED EMBODIMENT

Figure 1A:
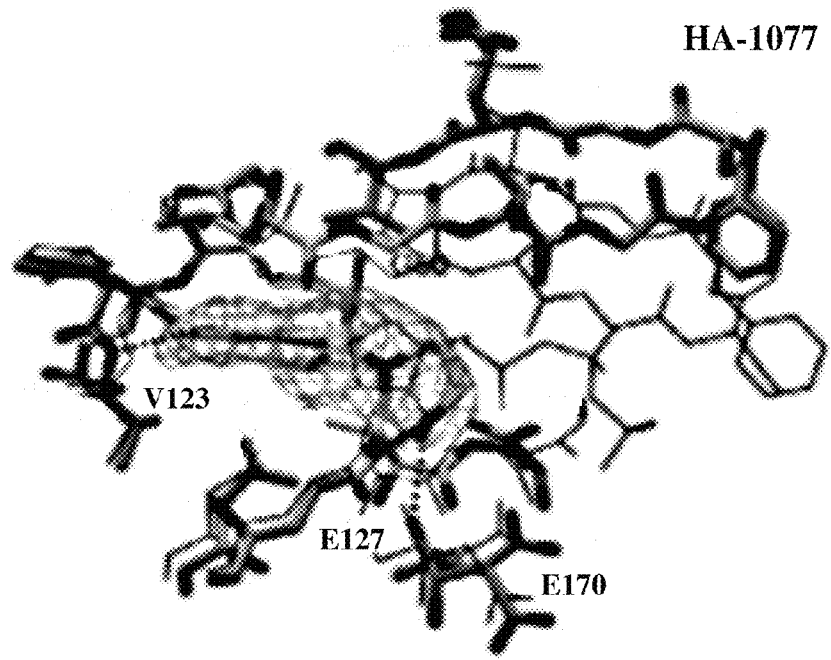
FIG. 1A is an image of the X-ray crystal of PKA with HA-1077 (Fasudil) bound to the ATP binding pocket.

The subject invention concerns compositions for blocking cancer cell growth or proliferation and/or inducing cancer cell death. Compositions of the invention are inhibitors of Rho-associated protein kinases. Compounds of the invention include piperazinyl pyridines, piperazinylmethylpyridines, piperazinyl ureas and carbamates, piperazinyl pyridines and quinoilines (including isoquinliones) as well as piperazinyl (including piperazinylmethyl)pyridines and quinolines (including isoquinolines).

In an illustrative embodiment, additional embodiments are discussed below, a compound of the invention has the general structure shown in formula I.

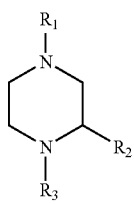

(I)

In a preferred embodiment, R1 is a heteroaryl such as pyridyl, quinolinyl or isoquinolinyl. R2 and R3 are individually selected from alkyl, alkoxy, cycloalkyl, cycloalkoxy, aryl, aryloxy, alkylcarbonyl, alkoxycarbonyl, cycloalkylcarbonyl, heteroalkyl, heterocycloalkyl, heterocycloalkylcarbonyl, heteroaryl, arylcarbonyl, heteroarylcarbonyl, aryloxycarbonyl, heteroaryloxycarbonyl, heterocycloalkoxy, or heterocycloalkoxycarbonyl, any of which can be optionally substituted with one or more of the following: any halogen, —CN, —COOH, =O, —OH, —NO2, —NH2, —N-alkyl, alkyl, alkoxy, cycloalkyl, cycloalkoxy, aryl, aryloxy, alkylcarbonyl, alkoxycarbonyl, cycloalkylcarbonyl, heteroalkyl, heterocycloalkyl, heterocycloalkylcarbonyl, heteroaryl, arylcarbonyl, heteroarylcarbonyl, aryloxycarbonyl, heteroaryloxycarbonyl, heterocycloalkoxy, or heterocycloalkoxycarbonyl; including salts thereof.

In a preferred embodiment, compounds of the invention have an R1 group selected from pyridyl, and quinolinyl moieties. For example, in one embodiment R1 is pyridyl. In another embodiment, R1 is a quinolinyl. In an exemplified embodiment, R1 is isoquinolinyl.

In another embodiment R2 is Bn, CH2OBn, Me, i-Pr, -Bu, OBn and Ph, or a salt thereof. In yet another embodiment, R3 is selected from the group consisting of CH3, Boc, H, COCH2NH2 or COCH2NHBoc (or other acceptable protecting group) or a salt thereof.

As used herein, alkyl means straight or branched chain, saturated or mono- or polyunsaturated hydrocarbon groups having from 1 to 20 carbon atoms and C1-x alkyl means straight or branched chain alkyl groups containing from one up to X carbon atoms wherein X is any positive integer. For example, C1-6 alkyl means straight or branched chain alkyl groups containing from one up to 6 carbon atoms. Alkoxy means an alkyl-O-group in which the alkyl group is as previously described. Cycloalkyl includes a nonaromatic monocyclic or multicyclic ring system, including fused and spiro rings, of from about three to about 10 carbon atoms. A cyclic alkyl may optionally be partially unsaturated. Alkylcarbonyl means a RC(O)— group where R is an alkyl group as previously described. Alkoxycarbonyl means an ROC(O)— group where R is an alkyl group as previously described. Cycloalkylcarbonyl means an RC(O)— group where R is a cycloalkyl group as previously described. Cycloalkoxycarbonyl means an ROC(O)— group where R is a cycloalkyl group as previously described. Heteroalkyl means a straight or branched-chain having from one to 20 carbon atoms and one or more heteroatoms selected from nitrogen, oxygen, or sulphur, wherein the nitrogen and sulphur atoms may optionally be oxidized, i.e., in the form of an N-oxide or an S-oxide. Heterocycloalkyl means a monocyclic or multicyclic ring system (which may be saturated or partially unsaturated), including fused and spiro rings, of about five to about 10 elements wherein one or more of the elements in the ring system is an element other than carbon and is selected from nitrogen, oxygen, silicon, or sulphur atoms. Cycloalkoxy means a cycloalkyl-O-group in which cycloalkyl is as defined herein.

Examples of saturated alkyl groups include, but are not limited to, methyl, ethyl, N-propyl, isopropyl, N-butyl, tert-butyl, isobutyl, sec-butyl, N-pentyl, N-hexyl, N-heptyl, and N-octyl. An unsaturated alkyl group is one having one or more double or triple bonds. Unsaturated alkyl groups include, for example, ethenyl, propenyl, butenyl, hexenyl, vinyl, 2-propynyl, 2-isopentenyl, 2-butadienyl, ethynyl, 1-propynyl, 3-propynyl, and 3-butynyl. Cycloalkyl groups include, for example, cyclopentyl, cyclohexyl, 1-cyclohexenyl, 3-cyclohexenyl, and cycloheptyl. Heterocycloalkyl groups include, for example, 1-piperidinyl, 2-piperidinyl, 3-piperidinyl, 3-morpholinyl, 4-morpholinyl, tetrahydrofuran-2-yl, tetrahydrofuran-3-yl, tetrahydrothien-2-yl, tetrahydrothien-3-yl, 1-piperazinyl, 2-piperazinyl, and 1,4-diazabicyclooctane.

Aryl means an aromatic monocyclic or multicyclic carbocyclic ring system, including fused and spiro rings, containing from about six to about 14 carbon atoms. Aryloxy means an aryl-O-group in which the aryl group is as described herein. Heteroaryl means a five to about a 14-membered aromatic monocyclic or multicyclic hydrocarbon ring system, including fused and spiro rings, in which one or more of the elements in the ring system is an element other than carbon and is selected from nitrogen, oxygen, silicon, or sulphur and wherein an N atom may be in the form of an N-oxide. Arylcarbonyl means an aryl-CO-group in which the aryl group is as described herein. Heteroarylcarbonyl means a heteroaryl-CO-group in which the heteroaryl group is as described herein and heterocycloalkylcarbonyl means a heterocycloalkyl-CO-group in which the heterocycloalkyl group is as described herein. Aryloxycarbonyl means an ROC(O)— group where R is an aryl group as previously described. Heteroaryloxycarbonyl means an ROC(O)— group where R is a heteroaryl group as previously described. Heterocycloalkoxy means a heterocycloalkyl-O— group in which the heterocycloalkyl group is as previously described. Heterocycloalkoxycarbonyl means an ROC(O)— group where R is a heterocycloalkyl group as previously described.

Aryl groups include, for example, benzyl, phenyl, indenyl, biphenyl, 1-naphthyl, 2-naphthyl, anthracenyl, and phenanthracenyl. Heteroaryl groups include, for example, 1-pyrrolyl, 2-pyrrolyl, 3-pyrrolyl, furyl, thienyl, imidazolyl, oxazolyl, isoxazolyl, thiazolyl, pyrazolyl, pyridyl, pyrimidyl, purinyl, indolyl, quinolinyl, isoquinolinyl, benzoquinolinyl, carbazolyl, and diazaphenanthrenyl. As used herein, halogen means the elements fluorine (F), chlorine (Cl), bromine (Br), and iodine (I).

The subject invention also contemplates compositions as described above, or a salt thereof, in a pharmaceutically acceptable carrier or diluent.

Salts of the compounds of the invention include those which are prepared with acids or bases, depending on the particular substituents present on the subject compounds described herein. Examples of a base addition salts include sodium, potassium, calcium, ammonium, or magnesium salt. Examples of acid addition salts include hydrochloric, hydrobromic, nitric, phosphoric, carbonic, sulphuric, and organic acids like acetic, propionic, benzoic, succinic, fumaric, mandelic, oxalic, citric, tartaric, maleic, and the like.

Peptides for use with the invention can be readily prepared using standard techniques known in the art, including chemical synthesis (Merrifield, 1963) and genetic engineering. Compounds of the invention can be synthesized or prepared from peptides using standard chemical procedures and materials.

The subject invention also concerns methods for inhibiting the growth or replication of a cell having abnormal growth or replication or whose growth or replication is uncontrolled, such as a cancer cell. In one embodiment, methods of the invention comprise inhibiting function of Rho-kinase, or an Rho-associated protein kinase, by contacting a cell with a compound of the invention wherein the compound is taken in or otherwise provided inside the cell. In one embodiment, the cell is a tumor cell, cancer cell, or a transformed cell. The cell can be a cell from a mammal, including human, dog, cat, and horse. The types of cells encompassed within the scope of the invention include, but are not limited to, cells of breast, kidney, mouth, larynx, esophagus, stomach, testis, cervix, head, neck, colon, ovary, lung, bladder, skin, muscle, pancreas, prostate, bone, eye, blood cells, and brain.

Methods of the invention also comprise inhibiting the function and/or growth and replication of a cell that is aberrantly or constitutively expressing Rho, Rho GTPase and/or Rho-kinase. In one embodiment, the method comprises contacting a cell with a compound of the invention. In one embodiment, the cell is a tumor cell, cancer cell, or a transformed cell. The cell can be a cell from a mammal, including human, dog, cat, and horse. The types of cells encompassed within the scope of the invention include, but are not limited to, cells of breast, kidney, mouth, larynx, esophagus, stomach, testis, cervix, head, neck, colon, ovary, lung, bladder, skin, muscle, pancreas, prostate, bone, eye, blood cells, and brain.

The subject invention also concerns methods for inducing apoptosis in a target cell. In one embodiment, the method comprises contacting a cell with a compound of the invention. In one embodiment, the cell is a tumor cell, cancer cell, or a transformed cell. The cell can be a cell from a mammal, including human, dog, cat, and horse. The types of cells encompassed within the scope of the invention include, but are not limited to, cells of breast, kidney, mouth, larynx, esophagus, stomach, testis, cervix, head, neck, colon, ovary, lung, bladder, skin, muscle, pancreas, prostate, bone, eye, blood cells, and brain.

Compounds of the invention can be delivered to a cell either through direct contact with the cell or via a carrier means. Carrier means for delivering compositions to cells are known in the art and include encapsulating the composition in a liposome moiety, and attaching the platinum complexes to a protein or nucleic acid that is targeted for delivery to the target cell. Published U.S. patent application Nos. 20030032594 and 20020120100 disclose amino acid sequences that can be coupled to a composition and that allows the composition to be translocated across biological membranes. Published U.S. patent application No. 20020035243 also describes compositions for transporting biological moieties across cell membranes for intracellular delivery.

The subject invention also concerns methods for treating tumors and oncological disorders in a patient. In one embodiment, an effective amount of a compound of the present invention is administered to a patient having an oncological disorder and who is in need of treatment thereof. The patient can be a human or other mammal having an oncological disorder. Means for administering and formulating a compound for administration to a patient are known in the art, examples of which are described herein. Oncological disorders that can be treated using the subject invention include cancer and/or tumors of the breast, kidney, mouth, larynx, esophagus, stomach, testis, cervix, head, neck, colon, ovary, lung, bladder, skin, muscle, pancreas, prostate, bone, eye, blood cells, and brain. The compounds of the invention can also be used to treat other disorders that are associated with aberrant or constitutive expression of Rho, Rho GTPase and/or Rho-kinase.

For the treatment of tumors and oncological disorders, the compounds of this invention can be administered to a patient in need of treatment alone, or in combination with other antitumor or anticancer substances and/or with radiation therapy and/or with surgical treatment to remove a tumor or cancerous tissue. These other substances or radiation treatments may be given at the same or different times as the compounds of this invention. For example, the compounds of the present invention can be used in combination with mitotic inhibitors such as taxol or vinblastine, alkylating agents such as cisplatin, cyclophosamide or ifosfamide, antimetabolites such as 5-fluorouracil or hydroxyurea, DNA intercalators such as adriamycin or bleomycin, topoisomerase inhibitors such as etoposide or camptothecin, antiangiogenic agents such as angiostatin, antiestrogens such as tamoxifen, and/or other drugs or antibodies that inhibit cancer cells, such as, for example, GLEEVEC (Novartis) and HERCEPTIN (Genetech), respectively.

Therapeutic application of the subject compounds, and compositions containing them, can be accomplished by any suitable therapeutic method and technique presently or prospectively known to those skilled in the art. The compounds can be administered by any suitable route known in the art including, for example, topical, oral, nasal, rectal, parenteral, subcutaneous, intramuscular, or intravenous routes of administration. Administration of the compounds of the invention can be continuous or at distinct intervals as can be readily determined by a person skilled in the art. The dosage to be administered to a patient can vary depending on several factors, including age, weight, and sex of the patient, and the type and severity of the disease. The ordinarily skilled clinician can determine suitable dosages following evaluation of the patient.

Compounds useful in the subject invention can be formulated according to known methods for preparing pharmaceutically useful compositions. Formulations are described in detail in a number of sources which are well known and readily available to those skilled in the art. For example, Remington's Pharmaceutical Science by E. W. Martin describes formulations which can be used in connection with the subject invention. In general, the compositions of the subject invention will be formulated such that an effective amount of the bioactive compound is combined with a suitable carrier in order to facilitate effective administration of the composition.

The compositions used in the present methods can also be in a variety of forms. These include, for example, solid, semi-solid, and liquid dosage forms, such as tablets, pills, powders, liquid solutions or suspension, suppositories, injectable and infusible solutions, and sprays. The preferred form depends on the intended mode of administration and therapeutic application. The compositions also preferably include conventional pharmaceutically acceptable carriers and diluents which are known to those skilled in the art. Examples of carriers or diluents for use with the subject compounds include, but are not limited to, water, saline, oils including mineral oil, ethanol, dimethyl sulfoxide, gelatin, cyclodextrans, magnesium stearate, dextrose, cellulose, sugars, calcium carbonate, glycerol, alumina, starch, and equivalent carriers and diluents, or mixtures of any of these. Formulations of the compounds of the invention can also comprise suspension agents, protectants, lubricants, buffers, preservatives, and stabilizers. To provide for the administration of such dosages for the desired therapeutic treatment, pharmaceutical compositions of the invention will advantageously comprise between about 0.1% and 45%, and especially, 1 and 15% by weight of the total of one or more of the compounds based on the weight of the total composition including carrier or diluent.

The compounds and compositions of the subject invention can also be administered utilizing liposome technology, slow release capsules, implantable pumps, and biodegradable containers. These delivery methods can, advantageously, provide a uniform dosage over an extended period of time.

The subject compounds can also be modified by the addition of chemical groups, such as PEG (polyethylene glycol). PEGylated peptides typically generate less of an immunogenic response and exhibit extended half-lives in vivo in comparison to peptides that are not PEGylated when administered in vivo. Methods for PEGylating proteins and peptides are known in the art (see, for example, U.S. Pat. No. 4,179,337). The subject compounds can also be modified to improve cell membrane permeability. In one embodiment, cell membrane permeability can be improved by attaching a lipophilic moiety, such as a steroid, to the compound. Other groups known in the art can be linked to compounds of the present invention.

The subject invention also concerns a packaged dosage formulation comprising in one or more containers at least one compound of the subject invention formulated in a pharmaceutically acceptable dosage. The package can contain discrete quantities of the dosage formulation, such as tablet, capsules, lozenge, and powders. The quantity of compound in a dosage formulation and that can be administered to a patient can vary from about 1 mg to about 2000 mg, more typically about 1 mg to about 500 mg, or about 5 mg to about 250 mg, or about 10 mg to about 100 mg.

Figure 1B:
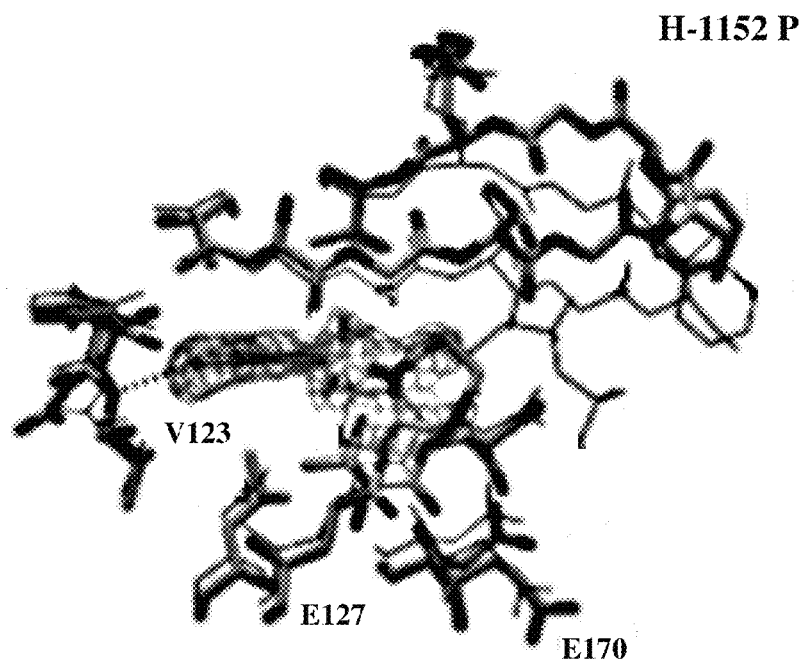
FIG. 1B is an image of the X-ray crystal of PKA with H-1152P bound to the ATP binding pocket.

FIGS. 1A and 1B show the X-ray crystal structure of PKA, used as the surrogate model for the Rho-kinase targeting ATP binding site of PKA (Breitenlehner, et. al.), with the known Rho-kinase inhibitors bound at the ATP binding pocket. Key interactions between the PKA ligands include backbone V123 with isoquinoline N (both HA-1077 (FIG. 1A) and H-1152 (FIG. 1B)), the backbone carbonyl oxygen E170 with homopiperazine N (HA-1077) and side chain oxygen E127 with homopiperazine N (HA-1077).

Figure 2:
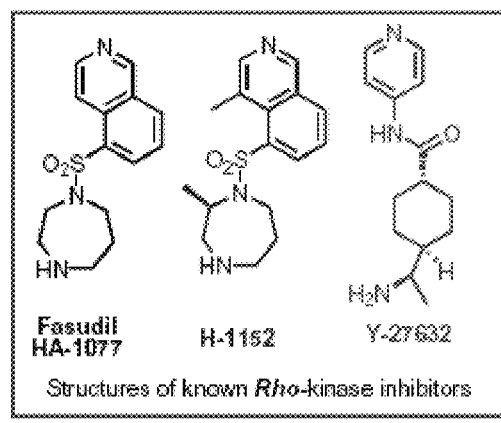
FIG. 2 is a series of chemical structures for known Rhokinase inhibitors; HA-1077 (Fasudil), H-1152 and Y-27632.
Figure 3A:
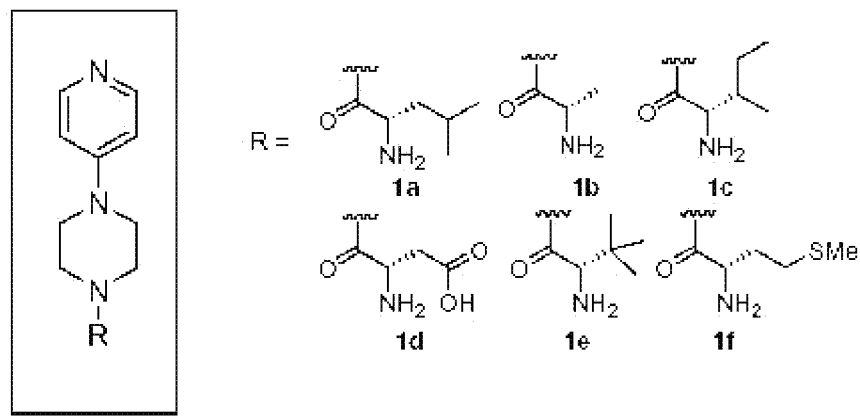
FIG. 3A is a series of chemical structures for 4-piperazinyl pyridines synthesized via acylations with various electrophiles.

The structures of known Rho-kinase inhibitors are shown in FIG. 2. A series of 4-piperazinyl pyridines (FIG. 3A) were synthesized via acylations with various electrophiles. The known inhibitors showed inhibitory activity at low µM concentrations but non showed sufficient inhibitory activity at 100 µM, as shown in FIG. 3B.

Figures 3B, 4A:
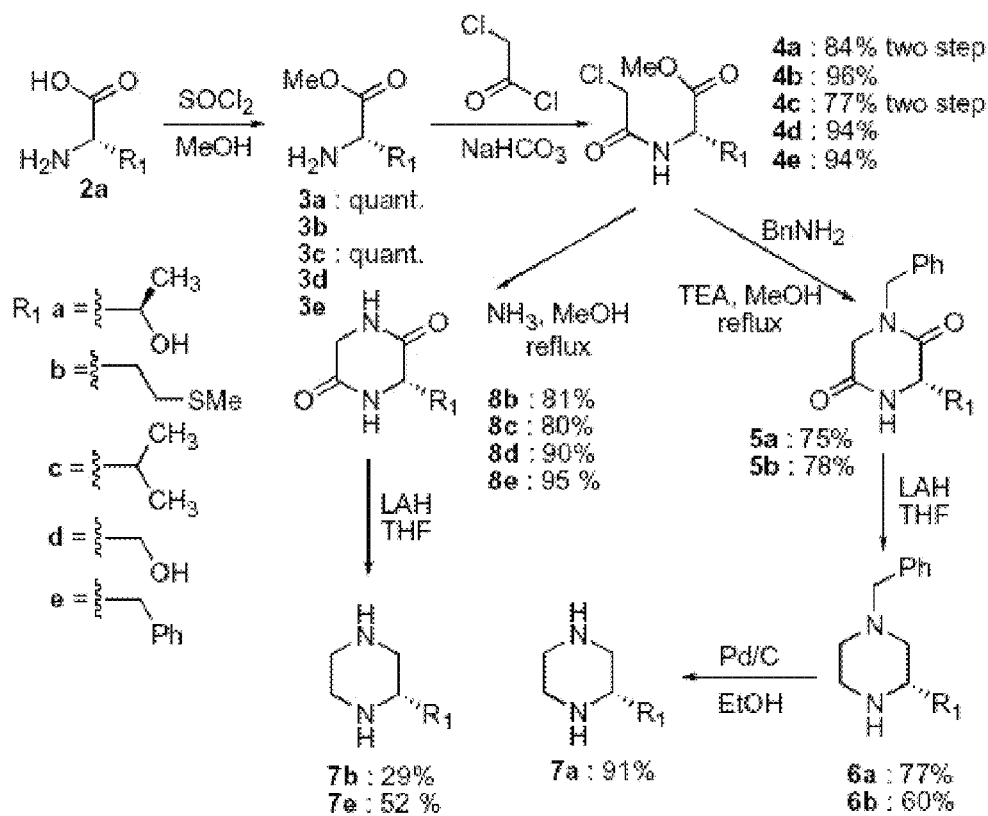
FIG. 3B is a table showing inhibitory activity of the compounds shown in FIG. 3A.
FIG. 4A is a schematic showing the synthesis of various 2-substituted piperazines.

One aspect invention includes the fast construction of a library of 2-substituted piperazines synthesized from a variety of dipeptides, as shown in FIG. 4A. Modifications from a previously reported protocol (see Breitenlechner. et al. Structure 2003, 11, 1595-1607; which is incorporated herein by reference) provide for the simple and straightforward synthesis of various 2-substituted piperazines (with optional selective protection/deprotection).

Figure 4B:
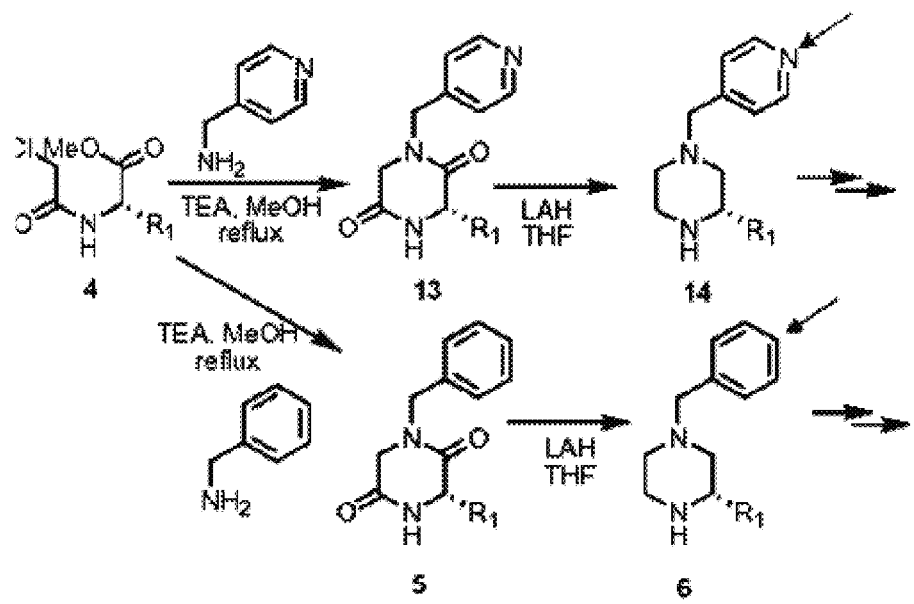
FIG. 4B is a schematic showing the synthesis of piperazinylmethylpyridines for use with the current invention.
Figure 5A:
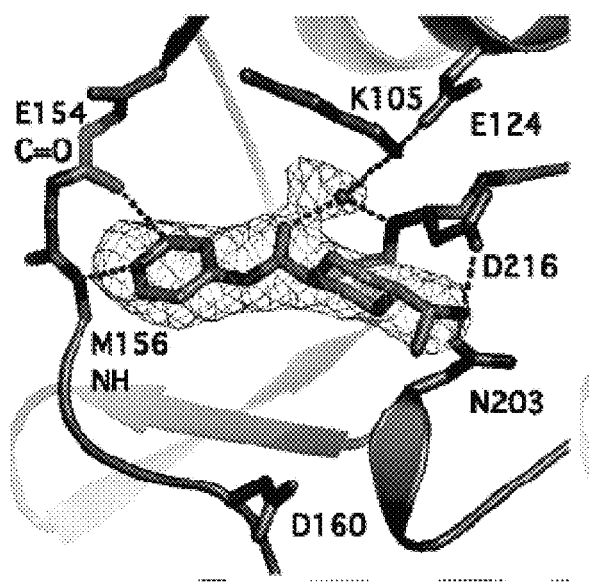
FIG. 5A represent the X-ray crystal structure of Rho kinase with N of Y-27632 bound to NH from M156.
Figure 5B:
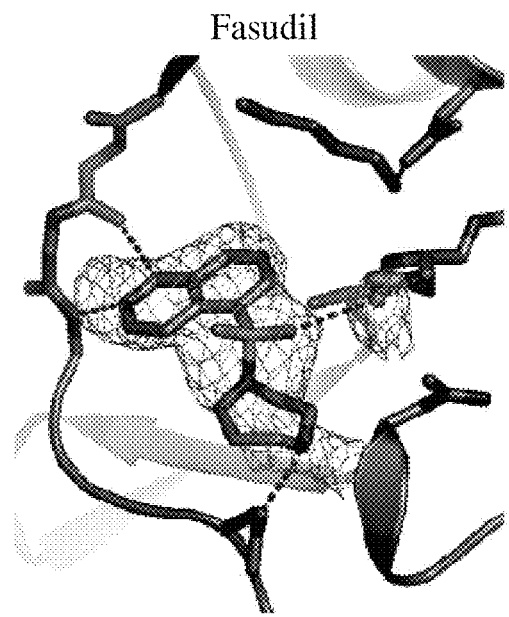
FIG. 5B represent the X-ray crystal structure of Rho kinase with N of HA-1077 (Fasudil) bound to NH from M156.
Figure 5C:
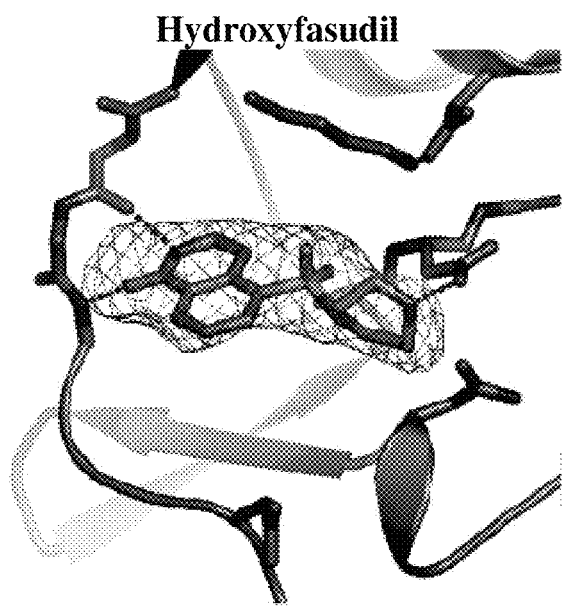
FIG. 5C represent the X-ray crystal structure of Rho kinase with N of Hydroxyfasudil bound to NH from M156.
Figure 5D:
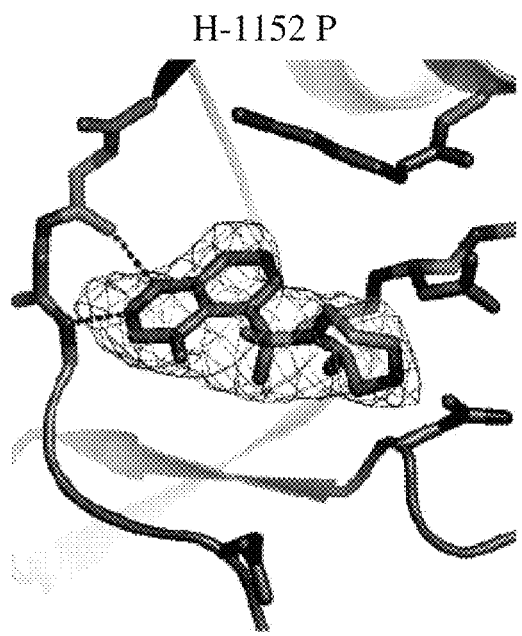
FIG. 5D represent the X-ray crystal structure of Rho kinase with N of H-1152P bound to NH from M156.

More accurately tailored scaffolds (piperanizylmethyl pyridine moieties) are shown in FIG. 1B. The compounds shown in FIG. 4B have less rigidity but fit into the deep ATP binding pocket and enable effective interaction with the backbone NH of M156 (FIGS. 5A-5D); (see also Liu, B. et. al. Syn. Comm. 2004, 34, 4111-4118, which is incorporated herein by reference, wherein R1=CH3). As it can be seen, the synthesis provides 3-4 moderate to high yielding linear steps from commercially available amino acids or their methyl esters. These findings demonstrate the important interaction between N from pyridine and NH from M156 by comparison with piperazinylmethyl benzene.

Referring again to FIGS. 5A-5B, the pyridine ring of Y-27632 (FIG. 5A) occupies the same space as the adenine six-membered ring in other kinase structures. It can also be seen the active site of ROCK and PKA are quite similar. Specifically, the consistent H-bond between backbone NH from M156 and N from pyridine or isoquinoline wing (M156=V123 from PKA).

Following are examples which illustrate procedures for practicing the invention. The disclosed compounds of one embodiment mimic the structures of known inhibitors and are diversified by the variation of hetero aromatic rings and a variety of piperazines. The disclosed designs provide significant benefit over the prior art. For example, piperazines are easily synthesized from dipeptides through the combination of suitable amino acids. Moreover, other bis-functional reagents (such as piperidine carboxylic acid) can be easily incorporated. Also, modifications through the remaining secondary amine afford specificity thereby allowing the discrimination from various kinases (i.e. similar ATP binding sites).

Figure 6A:
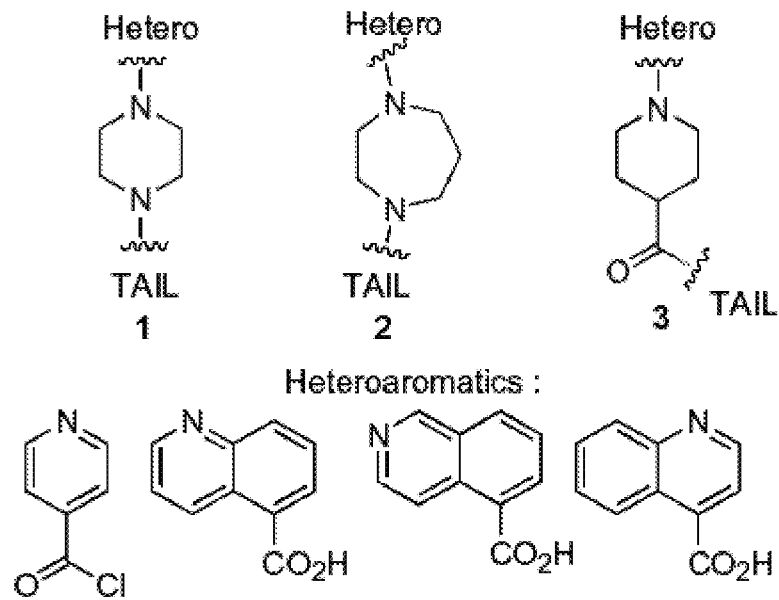
FIG. 6A shows the structures of piperazine, homopiperazine and isonipecotate which were selected among various commercially available bis-functional reagents for use with the current invention.
Figure 6B:
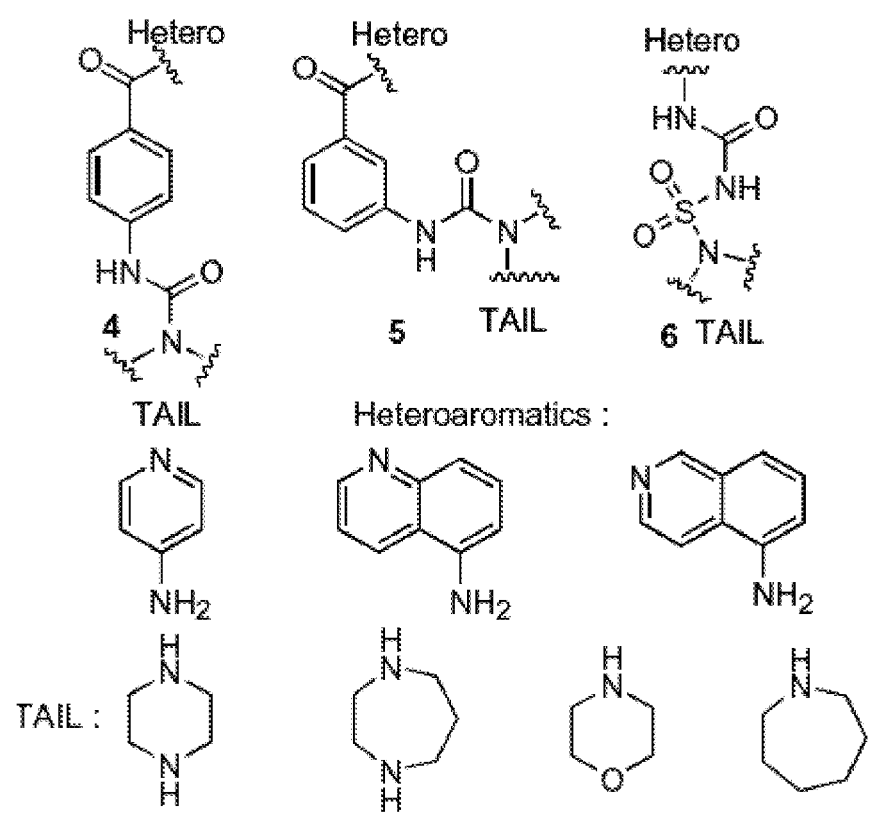
FIG. 6B shows the structures of isocyanato benzoylchloride and chlorosulfonyl isocyanate which were selected among various commercially available bis-functional reagents for use with the current invention.

The invention also provides for rapid screening using commercially available bis-functional reagents as key linkers or scaffolds. Such embodiments utilize selective and sequential coupling with heteroaromatic and tail groups. Illustrative, but not limiting, commercially available bis-functional reagents include piperazine, homopiperazine and isonipectotae (FIG. 6A) and chlorosulfonyl isocyanate (FIG. 6B). Combinations of amide, urea, carbamate and sulfonyl urea allow for a variety of scaffolds for use with the current invention.

EXAMPLE 1

Piperazinyl Pyridines or Quinolines

In a first embodiment, other embodiments are discussed below, a compound of the invention has the general structure shown in formula I.

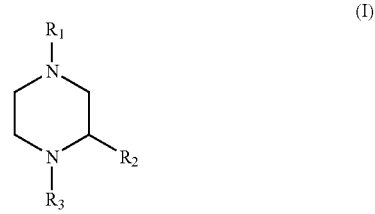

(I)

As previously described, R1 is a heteroaryl such as pyridyl, quinolinyl or isoquinolinyl. R2 and R3 are individually alkyl, alkoxy, cycloalkyl, cycloalkoxy, aryl, aryloxy, alkylcarbonyl, alkoxycarbonyl, cycloalkylcarbonyl, heteroalkyl, heterocycloalkyl, heterocycloalkylcarbonyl, heteroaryl, arylcarbonyl, heteroarylcarbonyl, aryloxycarbonyl, heteroaryloxycarbonyl, heterocycloalkoxy, or heterocycloalkoxycarbonyl, any of which can be optionally substituted with one or more of the following: any halogen, —CN, —COOH, =O, —OH, —NO2, —NH2, —N-alkyl, alkyl, alkoxy, cycloalkyl, cycloalkoxy, aryl, aryloxy, alkylcarbonyl, alkoxycarbonyl, cycloalkylcarbonyl, heteroalkyl, heterocycloalkyl, heterocycloalkylcarbonyl, heteroaryl, arylcarbonyl, heteroarylcarbonyl, aryloxycarbonyl, heteroaryloxycarbonyl, heterocycloalkoxy, or heterocycloalkoxycarbonyl; including salts thereof.

In a preferred embodiment, compounds of the invention have an R1 group selected from pyridyl, and quinolinyl moieties. For example, in one embodiment R1 is a pyridine. In another embodiment, R1 is a quinoline. In an exemplified embodiment, R1 is isoquinoline.

In another embodiment R2 is selected from the group consisting of Bn, CH2OBn, Me, i-Pr, -Bu, OBn and Ph, or a salt thereof. In yet another embodiment, R3 is selected from the group consisting of CH3, Boc, H, COCH2NH2 and COCH2NHBoc (or other acceptable protecting group) or a salt thereof.

The synthesis of compounds of this embodiment is shown in FIG. 1. As shown, pyridine, quinolines or isoquinolines were coupled with various piperazines through nucleophilic aromatic substitution or Hartwig Buchwald aryl amination. Piperazinyl isoquinolines exhibited notable inhibitory activity against Rho-kinase activity (i.e IC50=3.5 µM).

Examples of compositions of the invention are shown in Table 1 and have been designated numerically with an "IP-X-X" number. Compositions of the invention, such as those exemplified herein and designated as IP-IV-41 and IP-IV-49 are potent disrupters of active Rho-kinase and effectively disrupt Rho-kinase activity. FIG. 2 demonstrates the effectiveness of IP-IV-67 against ROCK1 in four assays.

TABLE 1

| COMPOUND | Number | % Inhibition |
|---|---|---|
|  | IP-IV-33<br>R = Bn | 47 |
|  | IP-IV-35<br>R = CH₂OBn | 54 |

TABLE 1-continued

| COMPOUND | Number | % Inhibition |
|---|---|---|
|  | IP-IV-47<br>R = Bn | 43 |
|  | IP-IV-49<br>R = CH₂OBn | 85 |
|  | IP-IV-41<br>R = Bn | 83<br>9.71 (@ 100 µM) |
|  | IP-IV-43<br>R = CH₂OBn | 49<br>4.73 (@ 100 µM) |
|  | IP-IV-67<br>R = Ph | 67<br>IC₅₀ = 3.5 µM |

TABLE 1-continued

| COMPOUND | Number | % Inhibition |
|---|---|---|
| 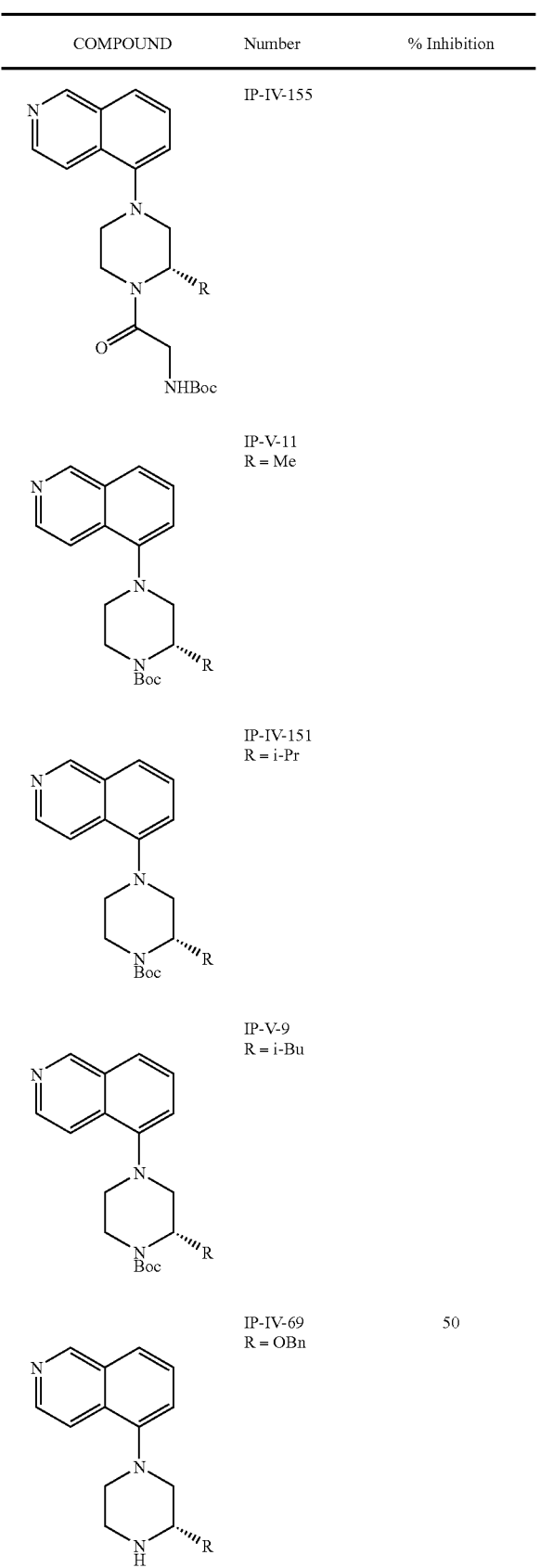 | IP-IV-155<br><br>IP-V-11<br>R = Me<br><br>IP-IV-151<br>R = i-Pr<br><br>IP-V-9<br>R = i-Bu<br><br>IP-IV-69<br>R = OBn | 50 |

TABLE 1-continued

| COMPOUND | Number | % Inhibition |
|---|---|---|
| 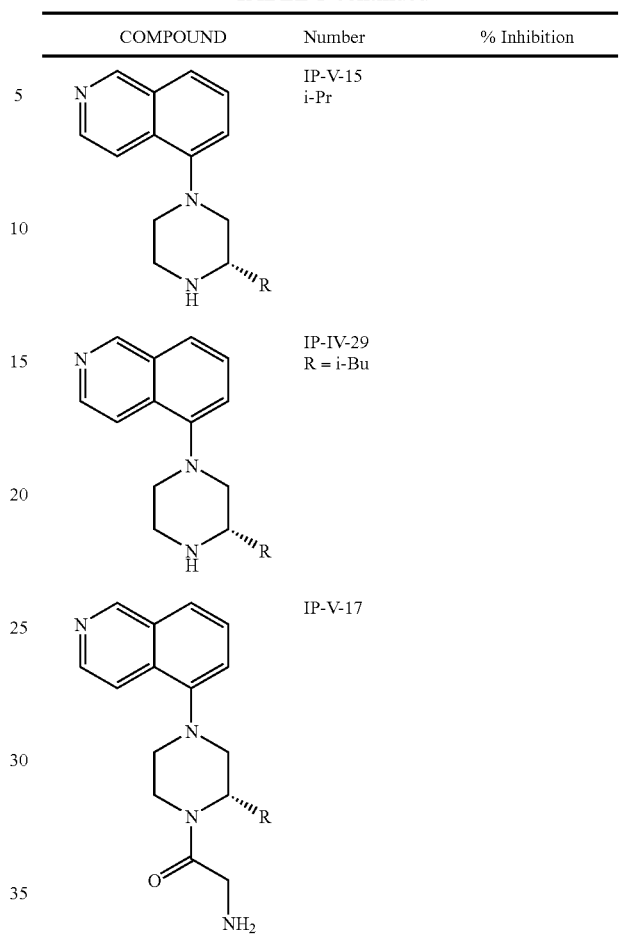 | IP-V-15<br>i-Pr<br><br>IP-IV-29<br>R = i-Bu<br><br>IP-V-17 | |

Figure 9:
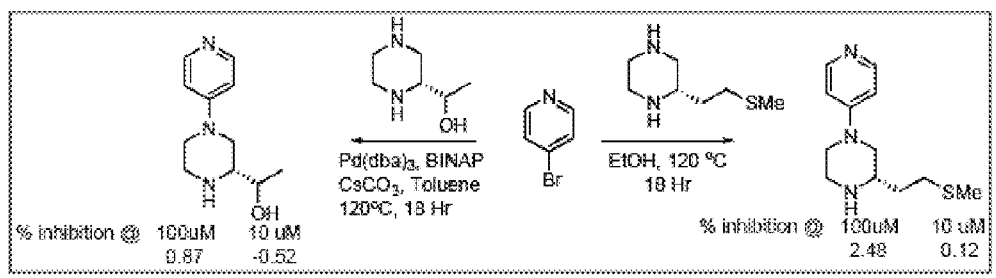
FIG. 9 is a schematic showing the synthesis of piperazinyl pyridines for use with the current invention.

FIG. 9 demonstrates the synthesis and associated inhibition of piperazinyl pyridines for use with the current invention.

EXAMPLE 2

Piperazinylmethyl Pyridines or Quinolines

In another embodiment, the Rho-protein associated kinase inhibitor has the structure shown in formula.

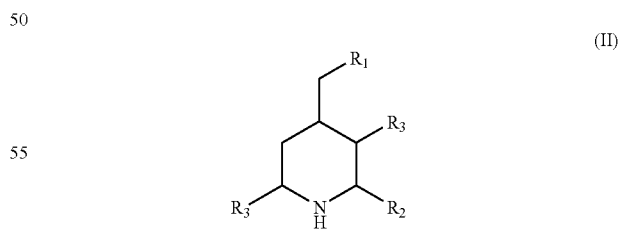

(II)

In this embodiment, $R_1$ is selected from the group consisting of pyridil, naphtyl and benzyl. $R_2$ and $R_3$ are individually selected from the group consisting of alkyl, alkoxy, cycloalkyl, cycloalkoxy, alkylcarbonyl, alkoxycarbonyl, cycloalkylcarbonyl, heteroalkyl, heterocycloalkyl, heterocycloalkylcarbonyl, heterocycloalkoxy, or heterocycloalkoxycarbonyl, any of which can be optionally substituted with one or more of the following: any halogen, —CN, —COOH, =O, —OH, —NO$_2$, —NH$_2$, —N-alkyl, alkyl, alkoxy, cycloalkyl, cycloalkoxy, aryl, aryloxy, alkylcarbonyl, alkoxycarbonyl, cycloalkylcarbonyl, heteroalkyl, heterocycloalkyl, heterocycloalkylcarbonyl, heteroaryl, arylcarbonyl, heteroarylcarbonyl, aryloxycarbonyl, heteroaryloxycarbonyl, heterocycloalkoxy, and heterocycloalkoxycarbonyl; or a salt thereof. Preferred embodiments are described below.

Figure 10A:
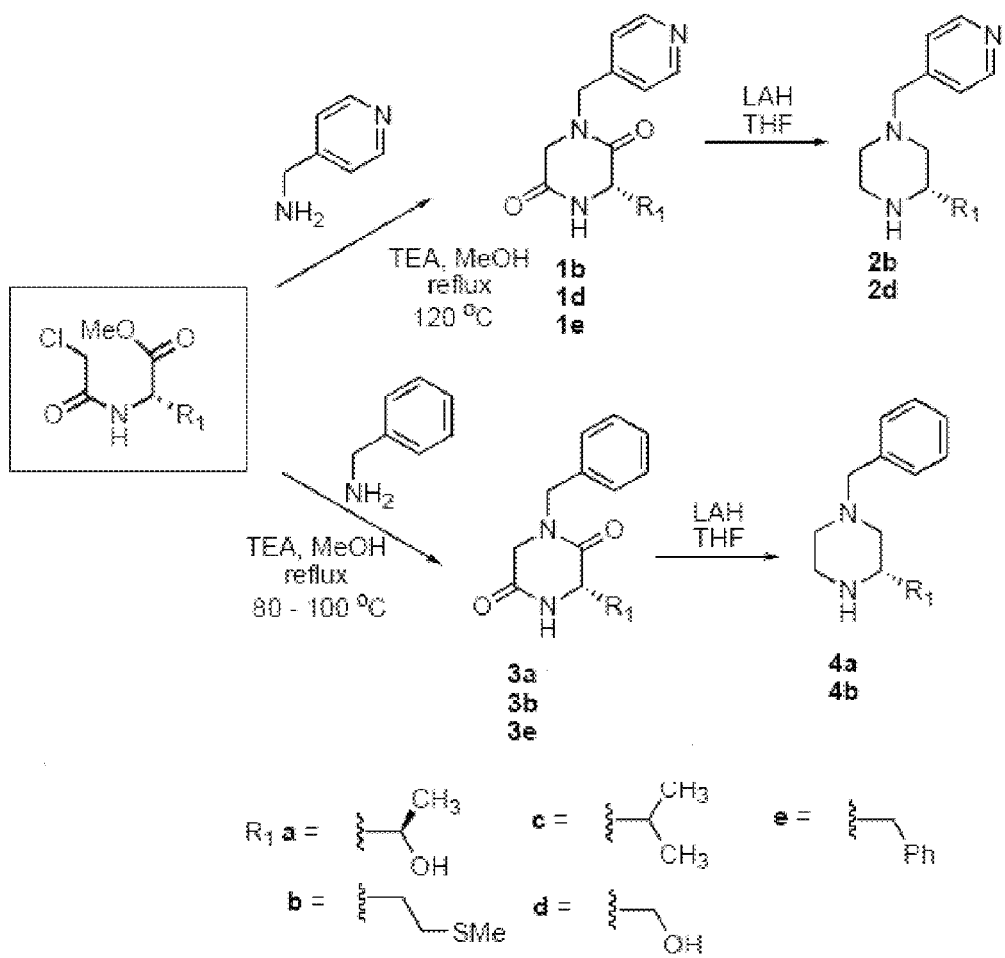
FIG. 10A is a schematic showing the synthesis of piperazinylmethylpyridines (including diketo-piperazinylmethylpyridines) for use with the current invention.
Figure 10B:
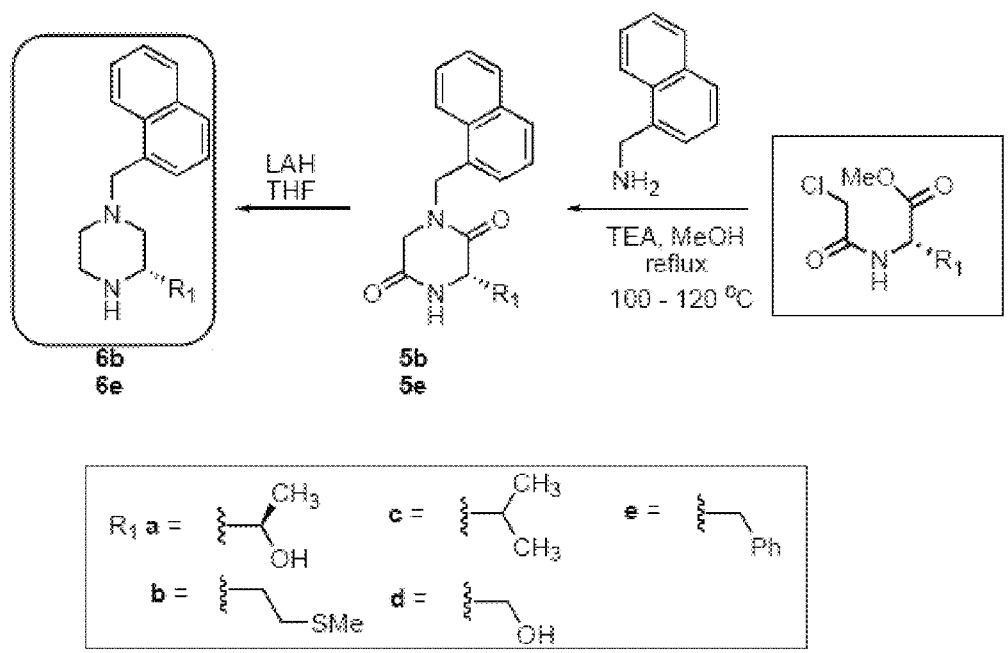
FIG. 10B is a schematic showing the synthesis of piperazinylmethyl moieties (including N-Naphtylmethyl-3-benzyl piperazine and diketo-piperazine) for use with the current invention.

In this embodiment, various diketopiperazines and piperazines were synthesized from alpha-chloro dipeptides (see FIGS. 10A and 10C). Piperazines showed superior inhibitory activity compared to diketopiperazines (see Table 2 below). N-Naphtylmethyl-3-benzyl piperazine (compound 6e, Table 2) showed particular effectiveness.

Examples of compositions of the invention are shown in Table 2 and have been designated numerically.

TABLE 2

| COMPOUND | Number | % Inhibition |
|---|---|---|
|  | 1b | 25<br>1.96 (@ 100 μM) |
|  | 1d | 45<br>1.73 (@ 100 μM) |
|  | 1e | ~20 |
|  | 2b | 36<br>4.35 (@ 100 μM) |

TABLE 2-continued

| COMPOUND | Number | % Inhibition |
|---|---|---|
|  | 2d | 20<br>3.73 (@ 100 μM) |
|  | 3a | 75 |
|  | 3b | 78 |
|  | 3e | 61<br>0.75 (@ 100 μM) |
|  | 4a | 77 |
|  | 4b | 60<br>0.53 (@ 100 μM) |

TABLE 2-continued

| COMPOUND | Number | % Inhibition |
|---|---|---|
| (naphthylmethyl piperazinedione with R₁) | 5b | 93<br>−1.48 (@ 100 μM) |
| (naphthylmethyl piperazinedione with R₁) | 5e | 71<br>−1.87 (@ 100 μM) |
| (naphthylmethyl piperazine with R₁) | 6b | 62<br>11.9 (@ 100 μM) |
| (naphthylmethyl piperazine with R₁) | 6e | 75<br>20.4 (@ 100 μM) |

R₁ a = —CH(OH)CH₃ b = —CH₂CH₂SMe c = —CH(CH₃)₂ d = —CH₂OH e = —CH₂Ph

EXAMPLE 3

Piperazinylmethyl Pyridines or Quinolines (Naphthyl Analogs)

In another embodiment, the Rho-protein associated kinase inhibitor has the general structure shown in formula III.

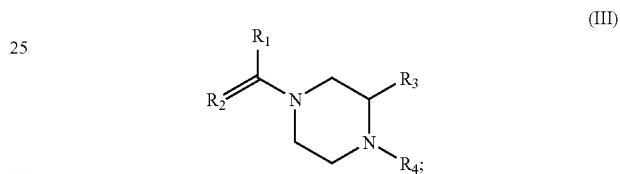

(III)

In the preferred embodiment R1 is a heteroaryl such as isoquinoline or quinoline. R2, R3 and R4 are individually selected from the group consisting of alkyl, alkoxy, cycloalkyl, cycloalkoxy, aryl, aryloxy, alkylcarbonyl, alkoxycarbonyl, cycloalkylcarbonyl, heteroalkyl, heterocycloalkyl, heterocycloalkylcarbonyl, heteroaryl, arylcarbonyl, heteroarylcarbonyl, aryloxycarbonyl, heteroaryloxycarbonyl, heterocycloalkoxy, or heterocycloalkoxycarbonyl, any of which can be optionally substituted with one or more of the following: any halogen, —CN, —COOH, =O, —OH, —NO2, —NH2, —N-alkyl, alkyl, alkoxy, cycloalkyl, cycloalkoxy, aryl, aryloxy, alkylcarbonyl, alkoxycarbonyl, cycloalkylcarbonyl, heteroalkyl, heterocycloalkyl, heterocycloalkylcarbonyl, heteroaryl, arylcarbonyl, heteroarylcarbonyl, aryloxycarbonyl, heteroaryloxycarbonyl, heterocycloalkoxy, and heterocycloalkoxycarbonyl; or a salt thereof.

Also in a preferred embodiment, as shown below, R2 is selected from the group consisting of methyl, benzyl, methylbenzyl, i-butane, i-propane and —COOH; R3 is selected from the group consisting of =O, H2, halo and (CH3)2; and R4 is CH3, Boc, H, COCH2NH2 and COCH2NHBoc; or a salt thereof.

Figure 11A:
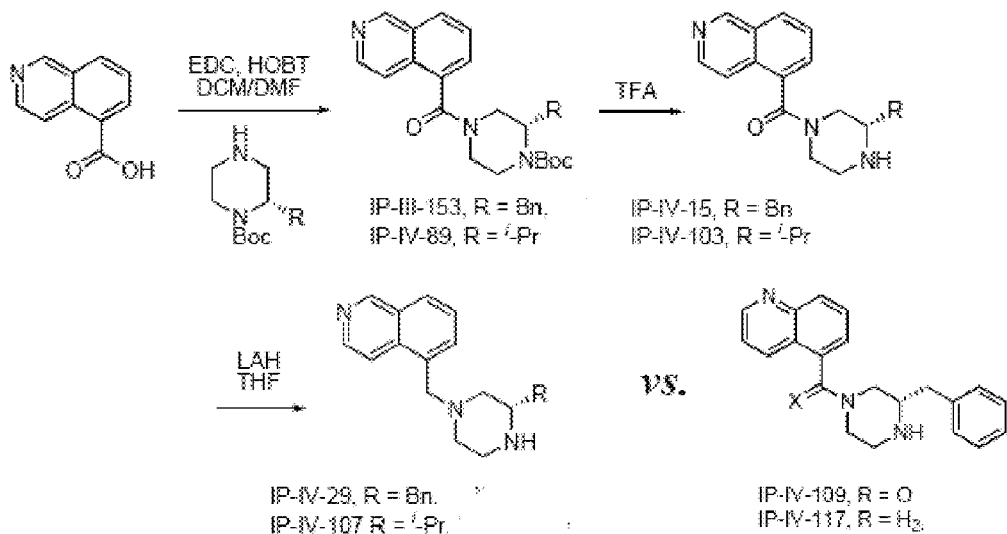
FIG. 11B is a schematic showing the synthesis of piperazinylmethylpyridines and isoquinolines for use with the current invention.
Figure 11B:
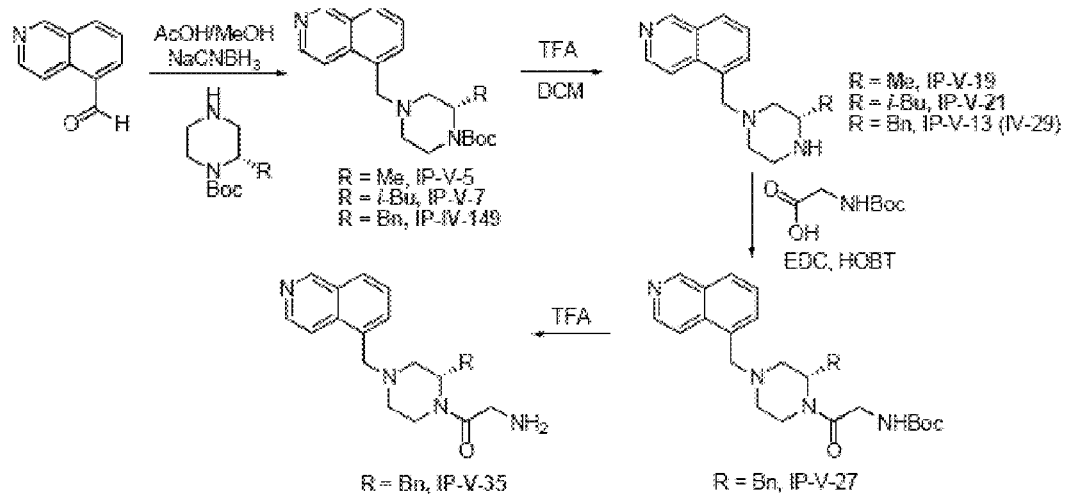
Figure 12:
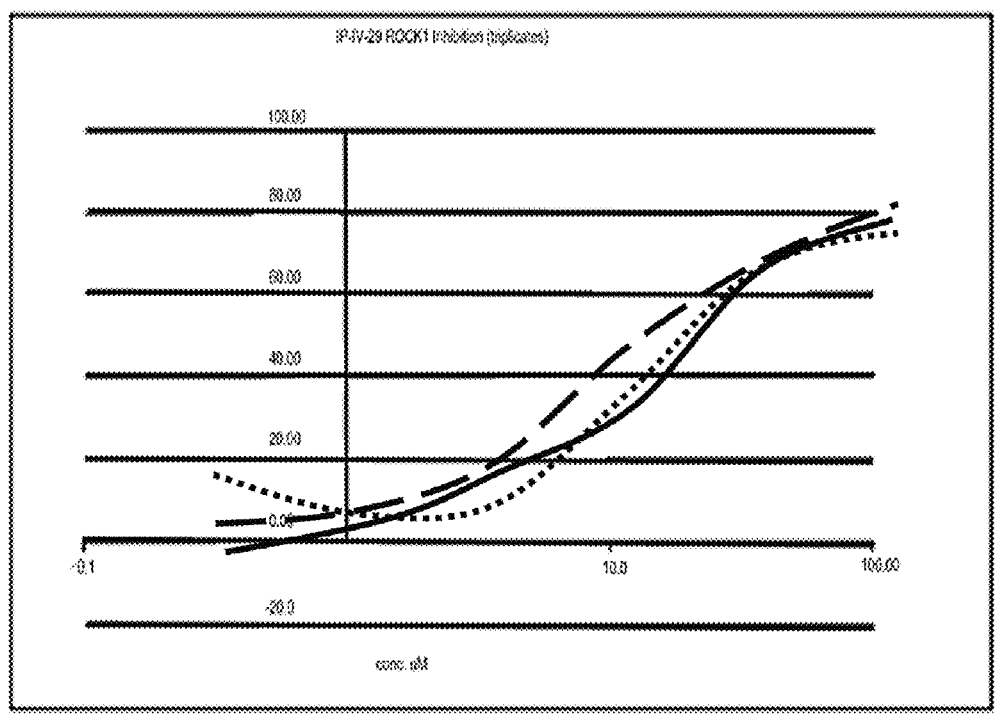
FIG. 12 is a graph showing the effectiveness of IP-IV-29 as a ROCK 1 inhibitor (results of 3 experiments shown).

The compounds according to this embodiment are shown in Table 3, below. Synthesis of the relevant compounds is shown in FIGS. 11A and 11B. Naphthyl analogs were selected for investigation and the naphthylene ring was substituted with isoquinoline. Surpisingly, a significant increase in effectiveness resulted from the use of isoquinoline rings (IC50=16-20 μM). It was also suprising that a marked difference existed between the amide (IP-IV-15, Table 3) and tert-amine moieties (IP-IV-29, see also FIG. 12). Quinoline derivatives also showed significant inhibitory activity.

Examples of compositions of the invention are shown in Table 3 and have been designated numerically with "IP-X-X" numbers.

TABLE 3
| COMPOUND | Number | Inhibition |
|---|---|---|
| 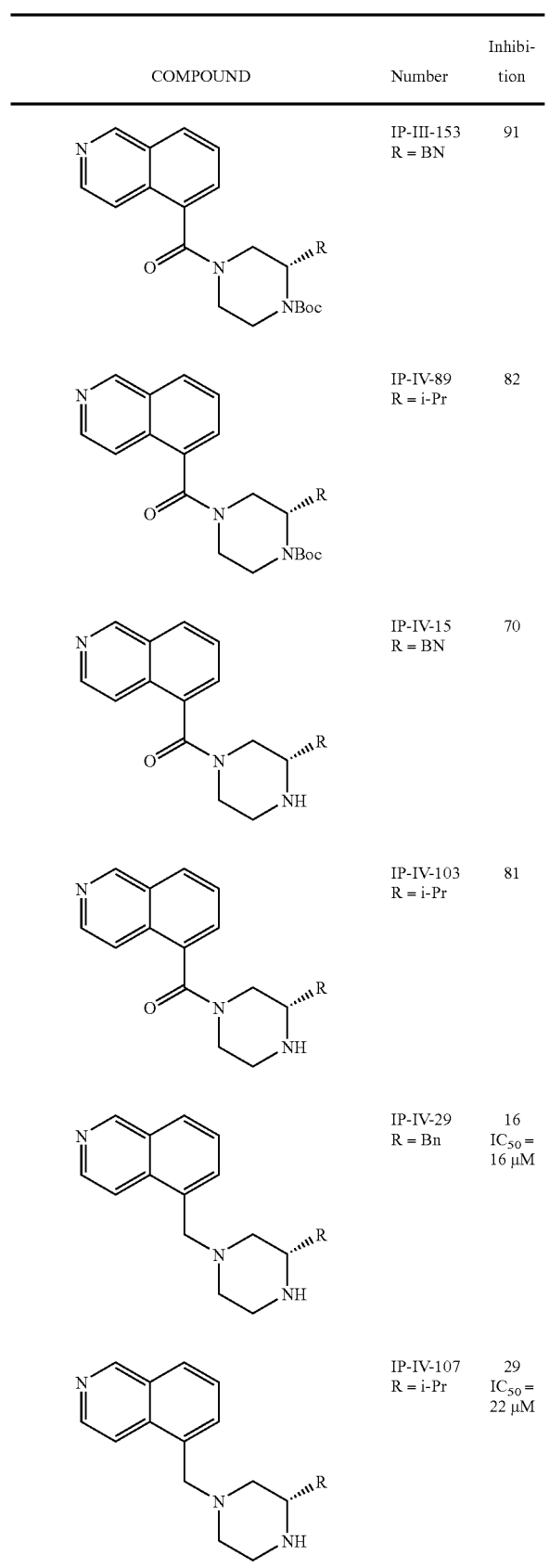 | IP-III-153 R = BN | 91 |
| | IP-IV-89 R = i-Pr | 82 |
| | IP-IV-15 R = BN | 70 |
| | IP-IV-103 R = i-Pr | 81 |
| | IP-IV-29 R = Bn | 16 IC$_{50}$ = 16 μM |
| | IP-IV-107 R = i-Pr | 29 IC$_{50}$ = 22 μM |
| 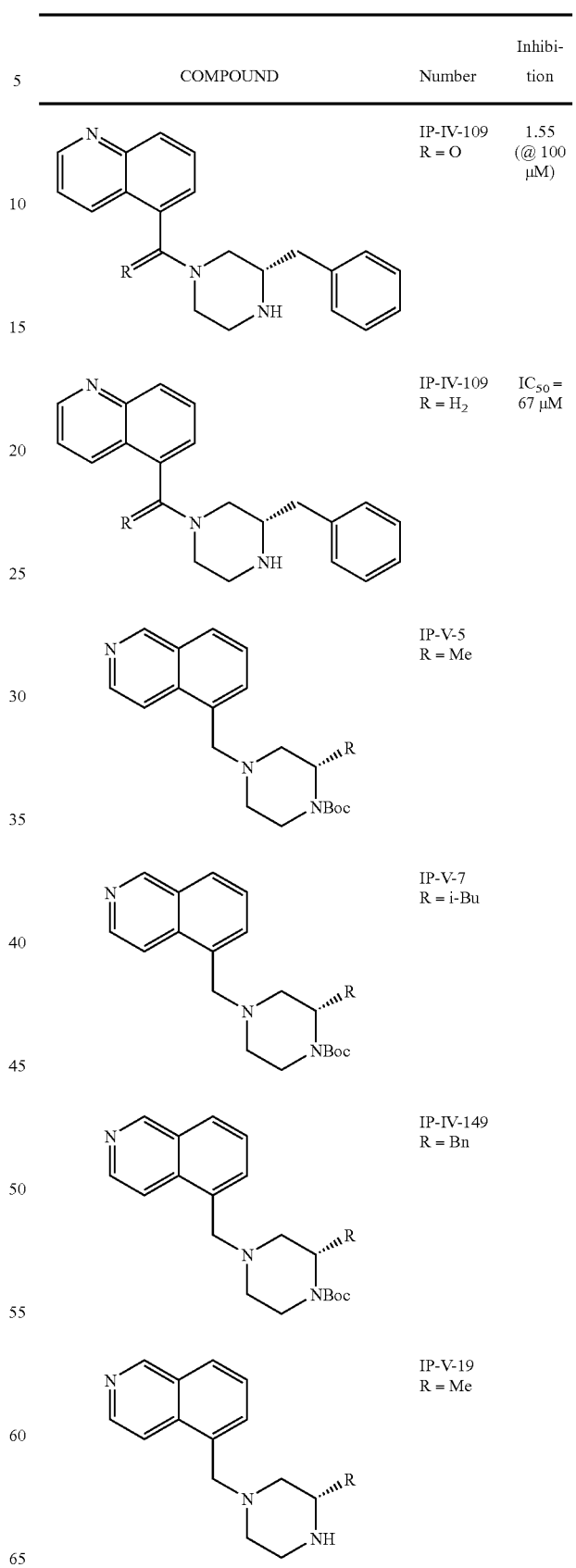 | IP-IV-109 R = O | 1.55 (@ 100 μM) |
| | IP-IV-109 R = H$_2$ | IC$_{50}$ = 67 μM |
| | IP-V-5 R = Me | |
| | IP-V-7 R = i-Bu | |
| | IP-IV-149 R = Bn | |
| | IP-V-19 R = Me | |

TABLE 3-continued

| COMPOUND | Number | Inhibition |
|---|---|---|
| | IP-V-21<br>R = i-Bu | |
| | IP-V-13<br>(IP-IV-29)<br>R = Me | |
| | IP-V-27<br>R = Bn | |
| | IP-V-35<br>R = Bn | |

EXAMPLE 4

Piperazinyl Ureas and Carbamates

In still another embodiment, the Rho-protein associated kinase inhibitor has the general structure shown in formula IV.

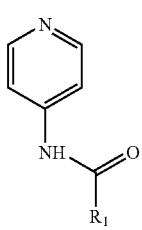

(IV)

R1 is selected from the group consisting of pyridine, piperazine and diazepine. R1 of the preferred embodiment for the pyridyl moieties is selected from the group consisting of the structures shown in formula V and formula VI.

(V)

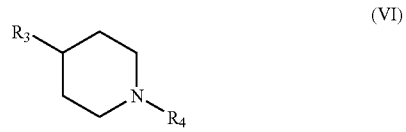

(VI)

In a general embodiment, R2 is selected from the group consisting of alkoxy, cycloalkoxy, aryloxy and aryloxycarbonyl; R3 is selected from the group consisting of NH and O; and R4 is selected from the group consisting of alkyl, alkoxy, cycloalkyl, cycloalkoxy, aryl, aryloxy, alkylcarbonyl, alkoxycarbonyl, cycloalkylcarbonyl, heteroalkyl, heterocycloalkyl, heterocycloalkylcarbonyl, heteroaryl, arylcarbonyl, heteroarylcarbonyl, aryloxycarbonyl, heteroaryloxycarbonyl, heterocycloalkoxy, or heterocycloalkoxycarbonyl, any of which can be optionally substituted with one or more of the following: any halogen, —CN, —COOH, =O, —OH, —NO2, —NH2, —N-alkyl, alkyl, alkoxy, cycloalkyl, cycloalkoxy, aryl, aryloxy, alkylcarbonyl, alkoxycarbonyl, cycloalkylcarbonyl, heteroalkyl, heterocycloalkyl, heterocycloalkylcarbonyl, heteroaryl, arylcarbonyl, heteroarylcarbonyl, aryloxycarbonyl, heteroaryloxycarbonyl, heterocycloalkoxy, and heterocycloalkoxycarbonyl; or a salt thereof.

In a preferred embodiment, however, R2 is selected from —COOH and —COOCH2CH3, R3 is selected from NH and O; and R4 is selected from Bn and H.

Figure 7:
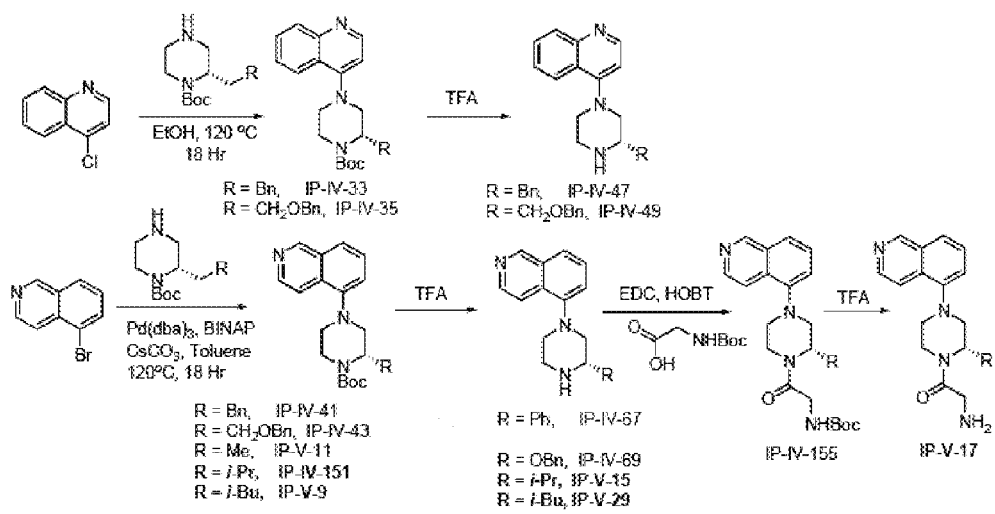
FIG. 7 is a schematic showing the synthesis of piperazinyl quinolines and isoquinolines for use with the current invention.
Figure 8:
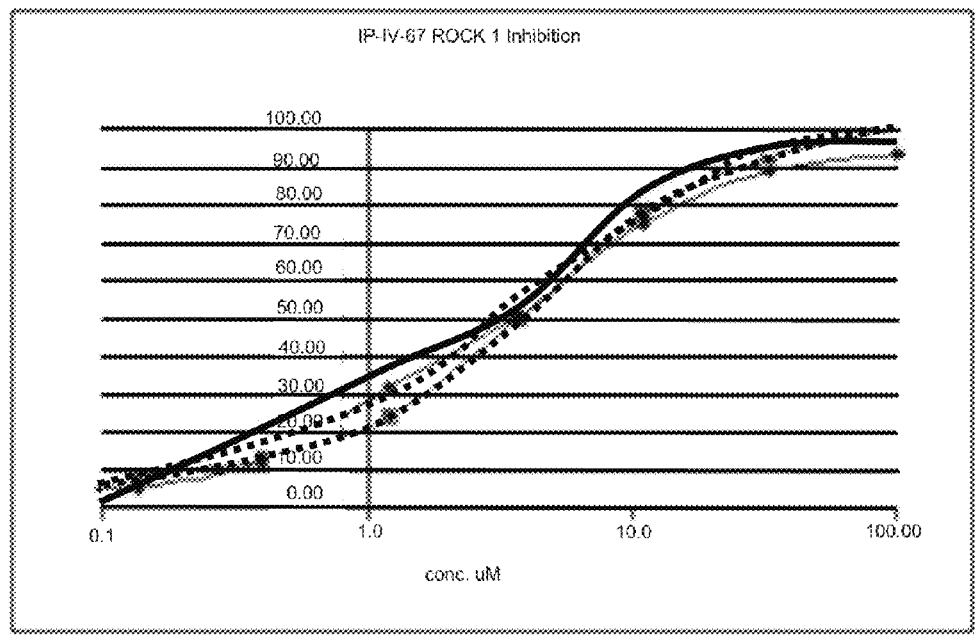
FIG. 8 is a graph showing the effectiveness of IP-IV-67 as a ROCK 1 inhibitor (results of 4 experiments shown).
Figure 13A:
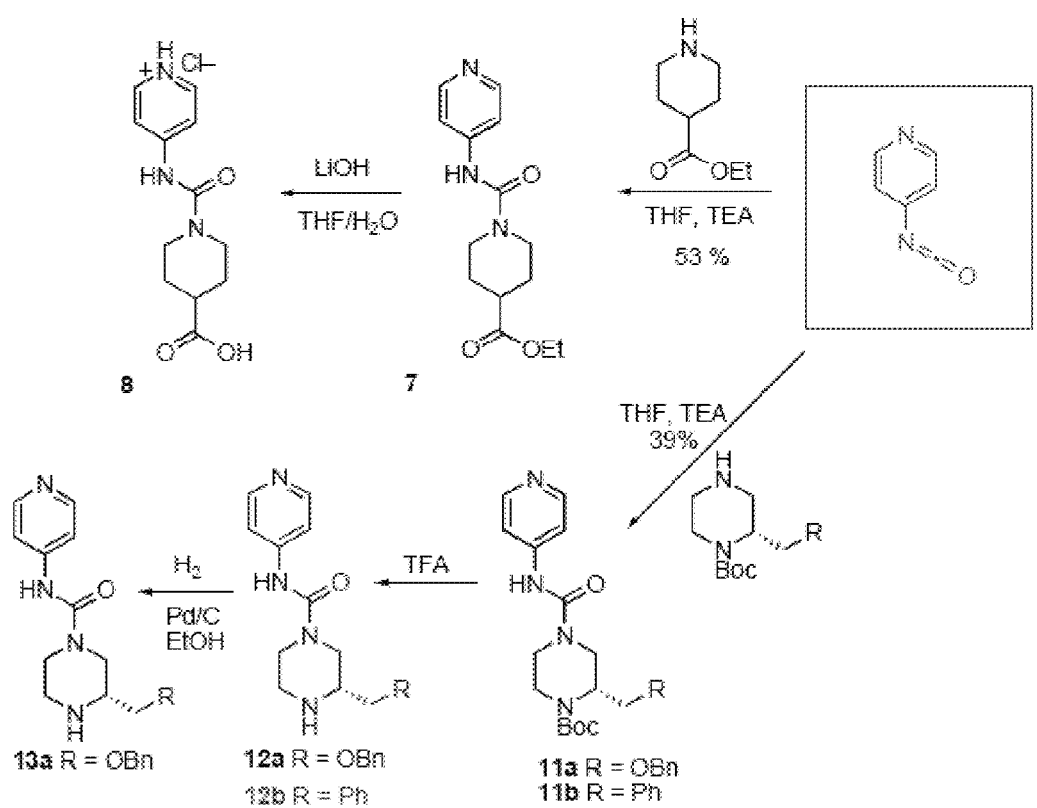
FIG. 13A is a schematic showing the synthesis of piperazinylmethyl ureas and carbamates for use with the current invention.
Figure 13B:
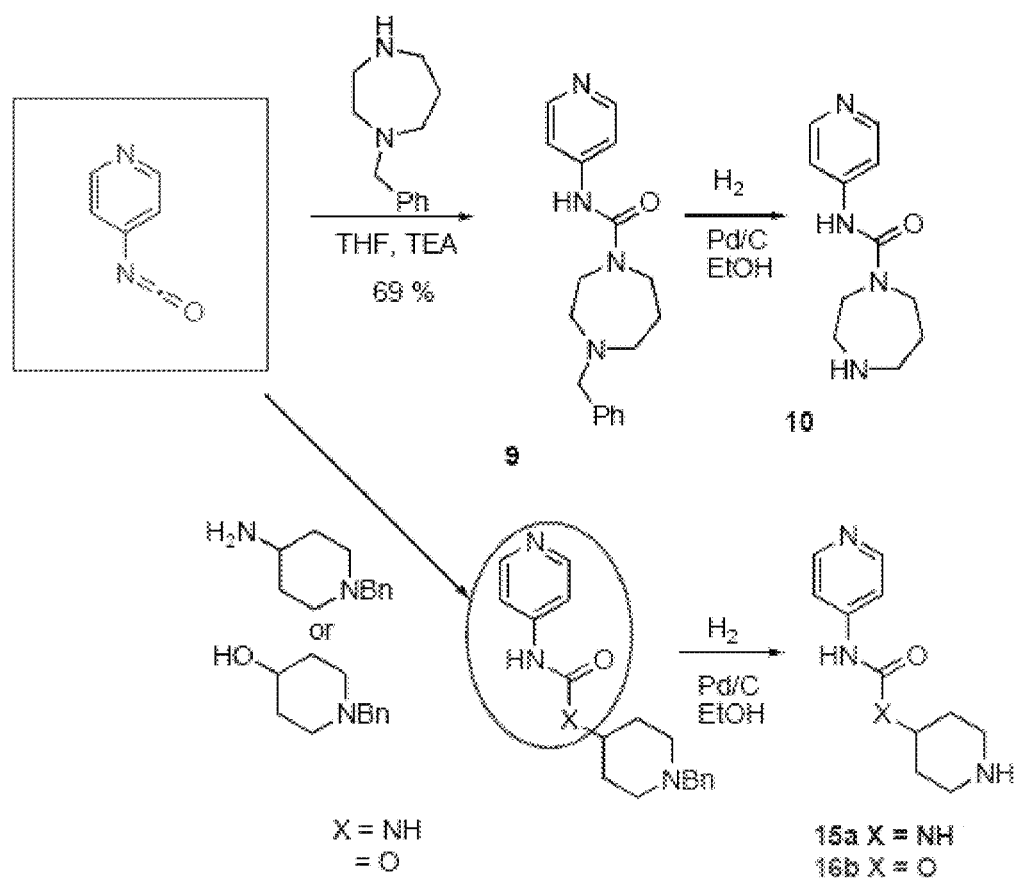
FIG. 13B is a schematic showing the synthesis of piperazinylmethylpyridines and isoquinolines for use with the current invention.
Figure 14A:
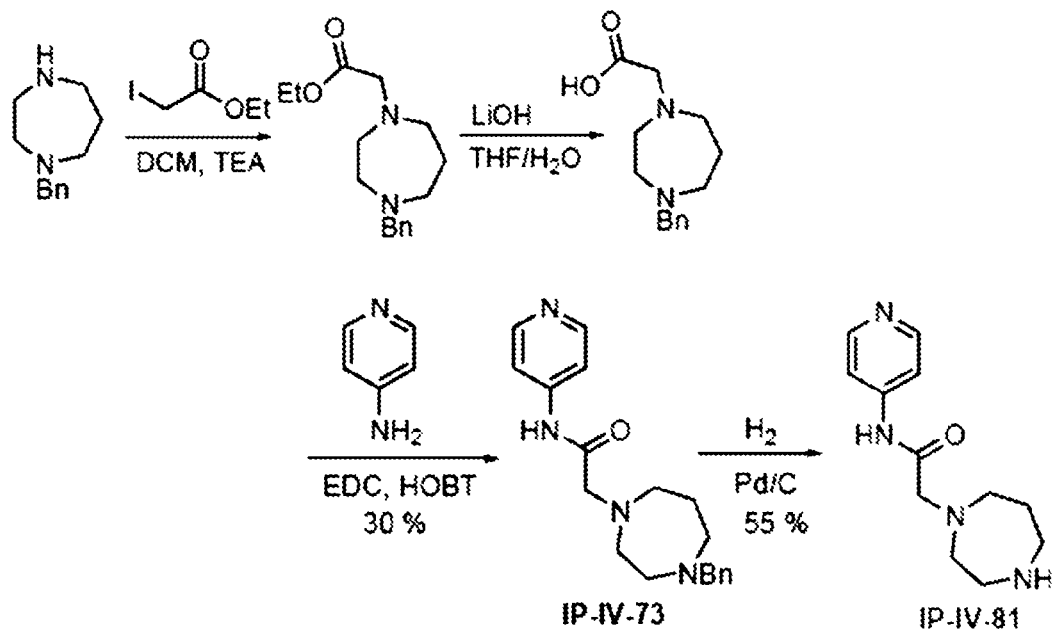
FIG. 14A is a schematic showing the synthesis of amines of the present invention using ureas.
Figure 14B:
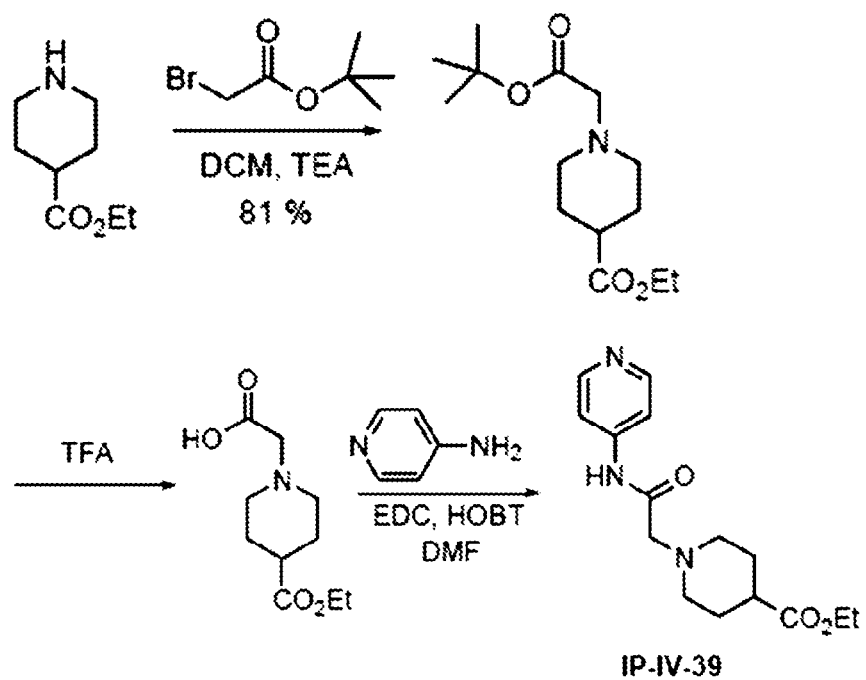
FIG. 14B is a schematic showing the synthesis of hybrid analogs (ureas and carbamates) for use with the current invention.
Figure 14C:
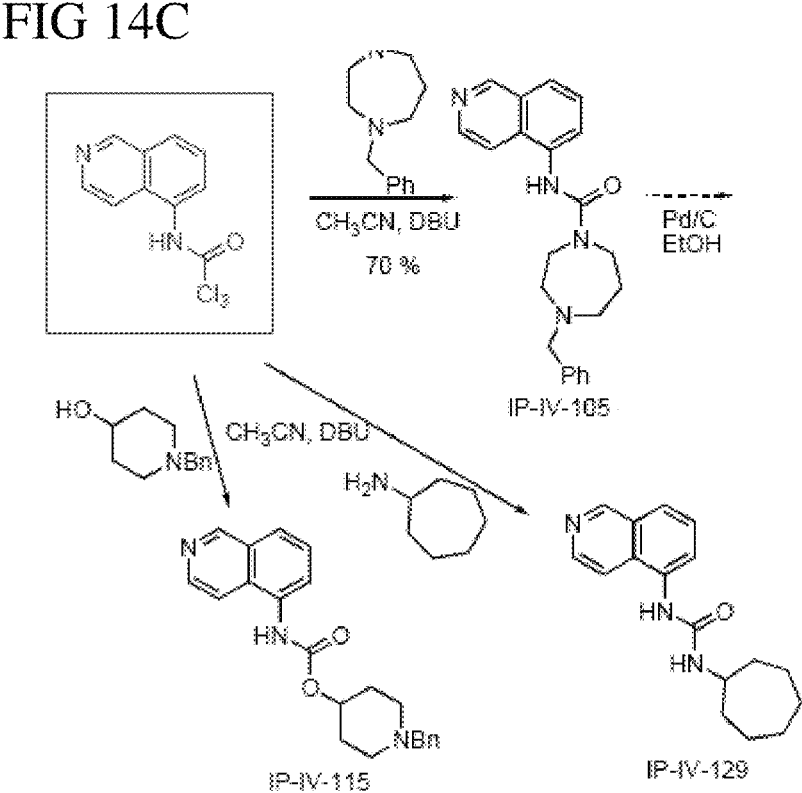
FIG. 14C is a schematic showing the synthesis of hybrid analogs (ureas and carbamates) for use with the current invention.
Figure 14D:
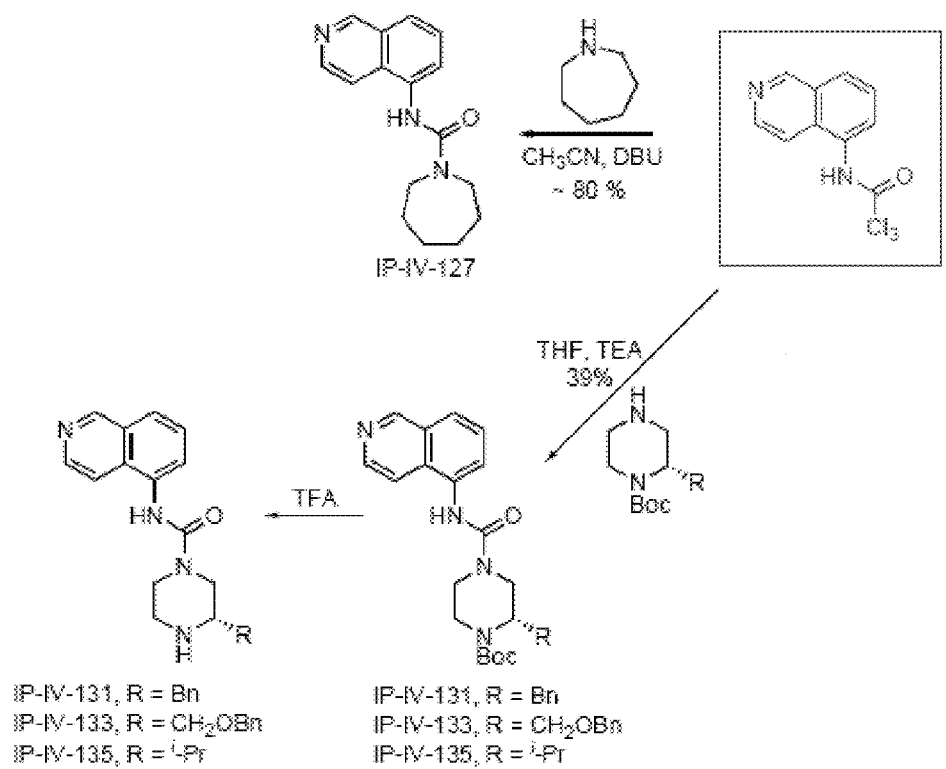
FIG. 14D is a schematic showing the synthesis of hybrid analogs (ureas and carbamates) for use with the current invention.

The synthesis of compounds of this embodiment is shown in FIGS. 13A and 13B. Compounds of this embodiment provide easy access in a one-step reaction from Isonictotinic acid (Curtis rearrangement) providing a straightforward reaction with various bis-functional amines or alcohol. While illustrative compounds are shown, other isocyanates including isoquinoline are contemplated. While compounds of this embodiment demonstrate Rho-kinase activity, compounds 12b (FIG. 7A) and 16b (FIG. 13B) demonstrated inhibitory activity at low micromolar concentrations (i.e. IC50=14 μM and 7.5 μM respectively).

Examples of compositions of the invention are shown in Table 4 and have been designated numerically. Compositions of the invention, such as those exemplified herein and designated as 12b and 16b are potent disrupters of active Rho-kinase and effectively disrupt Rho-kinase activity. While these compounds are generally more effective at lower micromolar concentrations, the effectiveness of these compounds may be influenced by the presence and the type, as well as the positioning, of functional groups on the aromatic ring.

TABLE 4

| COMPOUND | Number | Inhibition |
|---|---|---|
| (pyridine-NH-C(O)-piperidine-C(O)OEt) | 7 | 6.29 (@ 100 μM) |
| (pyridinium HCl-NH-C(O)-piperidine-COOH) | 8 | 1.59 (@ 100 μM) |
| (pyridine-NH-C(O)-N-benzyl-homopiperazine) | 9 | 21.0 (@ 100 μM) |
| (pyridine-NH-C(O)-homopiperazine-NH) | 10 | 16.7 (@ 100 μM) |

TABLE 4-continued

| COMPOUND | Number | Inhibition |
|---|---|---|
| (pyridine-NH-C(O)-piperazine-N-Boc, CH2R) | 11a R = OBn | 39 |
|  | 11b R = Ph | 40 (9.71 @ 100 μM) |
| (pyridine-NH-C(O)-piperazine-NH, CH2R) | 12a R = OBn | 89 (9.58 @ 100 μM) |
|  | 12b R = Ph | 43 (IC50 = 14 μM) |
| (pyridine-NH-C(O)-piperazine-NH, CH2R) | 13a R = OBn | 1.59 (@ 100 μM) |
| (pyridine-NH-C(O)-R-piperidine-NBn) | 14a R = NH | 25 (IC50 = 90 μM) |
|  | 14b R = O | 16 (IC50 = 56 μM) |
| (pyridine-NH-C(O)-X-piperidine-NH) | 15a R = NH | IC50 = 55 μM |
|  | 16b R = O | IC50 = 7.5 μM |

EXAMPLE 5

Hybrid Analogs of Ureas and Carbamates

The synthesis of compounds of this embodiment is shown in FIGS. 14A through 14D. In this embodiment, the isoquinolinyl areas and carbamates were synthesized stepwise with a trichloroacetyl chloride.

Examples of compositions of the invention are shown in Table 5 and have been designated numerically with an "IP-X-X" number. Compositions of the invention, such as those exemplified herein and designated as IP-IV135 and IP-IV-133 are potent disrupters of active Rho-kinase and effectively disrupt Rho-kinase activity. While these compounds are generally more effective at lower micromolar concentrations, the effectiveness of these compounds may be influenced by the presence and the type, as well as the positioning, of functional groups on the aromatic ring.

TABLE 5

| COMPOUND | Number (IP-IV-) | % Inhibition |
|---|---|---|
|  | 73 | 13.31 (@ 100 µM) |
|  | 81 | 30.61 (@ 100 µM) |
|  | 39 | −1.46 (@ 100 µM) |

TABLE 5-continued

| COMPOUND | Number (IP-IV-) | % Inhibition |
|---|---|---|
|  | 105 | −0.85 (@ 100 µM) |
|  | 127 |  |
|  | 131 R = Bn | 60 |
|  | 133 R = CH$_2$OBn | 66 |
|  | 135 R = i-Pr | 54 |
|  | 131 R = Bn | 58 |
|  | 133 R = CH$_2$OBn | 76 |
|  | 135 R = i-Pr | 90 |

TABLE 5-continued

| COMPOUND | Number (IP-IV-) | % Inhibition |
|---|---|---|
| | 115 | 50 |
| | 129 | 50 |

EXAMPLE 6

Piperidinyl Pyridines-Isonipecotate

Figure 15:
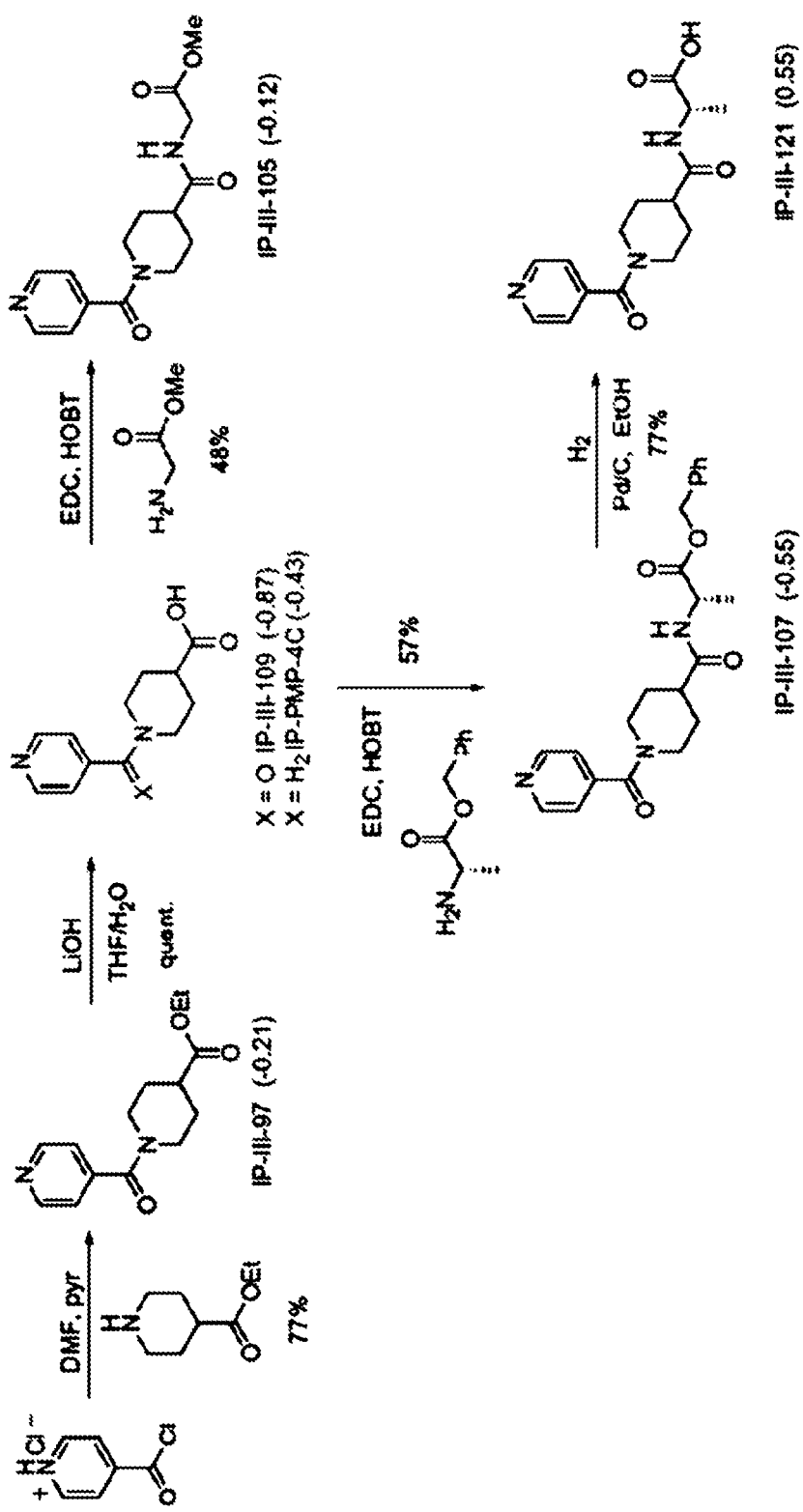
FIG. 15 is a schematic showing the synthesis of piperidinyl pyridines (isonipecotate) for use with the current invention.

The synthesis of compounds of this embodiment is shown in FIG. 15. In this embodiment, simple isonicotinoyl was coupled with isonipecotate to form piperidinyl-pyridines. In the example shown in FIG. 15, the bis-functional isonipecotic acid was used instead of bis-functional piperidines. The process provides straightforward reactions with moderate to high yields in each step. Results of inhibition are shown in parenthesis, no significant change was noticed by the modification of amide to amine. Improved inhibition is possible, however, by the coupling of isonipecotate with other aromatic rings (including isoquinolines) as well as other amino acid tails.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween. Now that the invention has been described,

What is claimed is:
1. A compound having the structure shown in formula I:

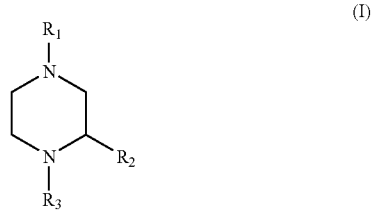

wherein $R_1$ is pyridyl;
wherein $R_2$ is selected from the group consisting of Bn, $CH_2OBn$, i-propane, butane, OBn, Ph, H, $CH_2CH_2SMe$, $CH(CH_3)OH$, and a salt thereof;
wherein $R_3$ is selected from the group consisting of $CH_3$, butoxycarbonyl, H,

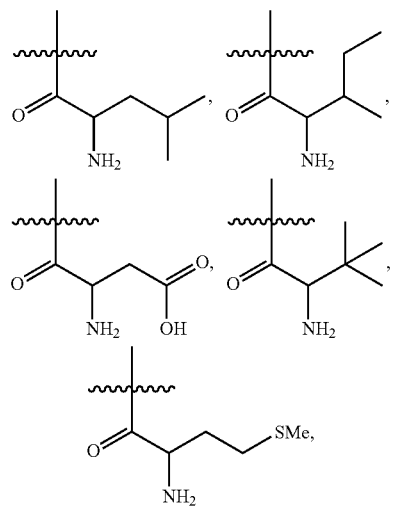

$COCH_2NH$-y, H, and a salt thereof,
where y is a protecting group; and
where $R_2$ and $R_3$ are not concurrently H.

2. The compound of claim 1 wherein $R_2$ is selected from the group consisting of Bn, $CH_2OBn$, Me, i-Pr, -Bu, OBn and Ph, and a salt thereof.

3. The compound of claim 1 wherein $R_3$ is selected from the group consisting of $CH_3$, butoxycarbonyl, H, and $COCH_2NHBoc$, and a salt thereof.

4. A compound having the structure shown in formula II;

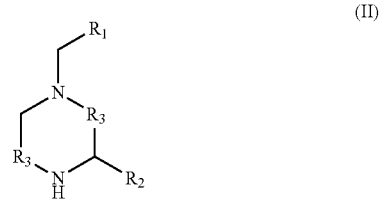

wherein $R_1$ is selected from the group consisting of pyridyl and methylpyridyl;
wherein $R_2$ is selected from the group consisting of $CH(CH_3)OH$, $CH_2Ph$, $CH_2CH_2SMe$, $CH_2OH$, butyl, i-butyl, propyl, i-propyl, and a salt thereof; and $R_3$ is selected from the group consisting of C=O, $CH_2$, CH-halo, and $C(CH_3)_2$.

5. The compound of claim 4 wherein $R_1$ is methylpyridyl.

6. The Compound of claim 4 wherein $R_2$ is selected from the group consisting of $CH(CH_3)OH$, butyl, i-butyl, propyl, i-propyl and $(CH_2)_2SCH_3$; and wherein $R_3$ is selected from the group consisting of C=O, $CH_2$, CH-halo, and $C(CH_3)_2$.

7. The compound of claim 4 selected from the group consisting of:

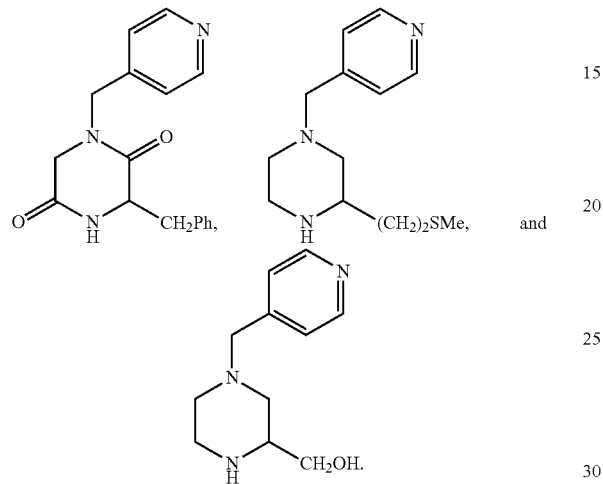

* * * * *